(12) United States Patent
Fujimura et al.

(10) Patent No.: US 8,684,528 B2
(45) Date of Patent: Apr. 1, 2014

(54) FUNDUS ANALYZING APPARTUS AND FUNDUS ANALYZING METHOD

(75) Inventors: Takashi Fujimura, Tokyo (JP); Hiroyuki Aoki, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 235 days.

(21) Appl. No.: 13/387,497

(22) PCT Filed: Jul. 14, 2010

(86) PCT No.: PCT/JP2010/004581
§ 371 (c)(1),
(2), (4) Date: Jan. 27, 2012

(87) PCT Pub. No.: WO2011/013315
PCT Pub. Date: Feb. 3, 2011

(65) Prior Publication Data
US 2012/0120368 A1    May 17, 2012

(30) Foreign Application Priority Data
Jul. 30, 2009    (JP) ................................. 2009-177420

(51) Int. Cl.
*A61B 3/12*    (2006.01)
*A61B 3/10*    (2006.01)

(52) U.S. Cl.
CPC . *A61B 3/12* (2013.01); *A61B 3/102* (2013.01); *A61B 3/1005* (2013.01); *G06T 2207/10101* (2013.01); *G06T 2207/30041* (2013.01)
USPC .......................................... 351/206; 351/246

(58) Field of Classification Search
CPC ........ A61B 3/12; A61B 3/102; A61B 3/1005; G06T 7/0012; G06T 2207/10101; G06T 2207/30041
USPC .................................................. 351/206, 246
See application file for complete search history.

(56) References Cited

U.S. PATENT DOCUMENTS 6,377,349 B1    4/2002    Fercher
7,345,770 B2    3/2008    Chan et al.
(Continued)

FOREIGN PATENT DOCUMENTS

JP    09-276232 A    10/1997
JP    11-325849 A    11/1999
(Continued)

OTHER PUBLICATIONS

International Search Report for PCT/JP2010/004581; mail date Aug. 10, 2010.

*Primary Examiner* — Zachary Wilkes
(74) *Attorney, Agent, or Firm* — Pearne & Gordon LLP

(57) ABSTRACT

A fundus analyzing apparatus 1 performs OCT measurements of a fundus Ef and generates multiple tomographic images that each depict layer structures of the fundus Ef. Each formed tomographic image is stored in a storage 212. Based on the pixel values of the pixels of each tomographic image, the layer-region identifying part 233 identifies the layer region corresponding to the pigment layer of the retina. Based on the shape of the layer region, the curve calculator 234 obtains a convex standard curve in the direction of depth of the fundus Ef. Based on the layer region and the standard curve, a protrusion-region identifying part 235 identifies protrusion regions where the layer region protrudes in the opposite direction from the direction of depth of the fundus Ef. A morphological-information generating part 236 generates morphological information representing the morphology (number, size, distribution, etc.) of the protrusion regions.

26 Claims, 11 Drawing Sheets

(56) References Cited

U.S. PATENT DOCUMENTS

| | | | |
|---|---|---|---|
| 8,442,286 B2 * | 5/2013 | Imamura et al. | 382/128 |
| 2010/0220914 A1 * | 9/2010 | Iwase et al. | 382/131 |

FOREIGN PATENT DOCUMENTS

| | | |
|---|---|---|
| JP | 2002-139421 A | 5/2002 |
| JP | 2006-153838 A | 6/2006 |
| JP | 2007-024677 A | 2/2007 |
| JP | 2008-073099 A | 4/2008 |
| JP | 2008-272256 A | 11/2008 |
| JP | 2008-295804 A | 12/2008 |
| JP | 2009-089792 A | 4/2009 |
| JP | 2010-35607 A | 2/2010 |
| JP | 2010-94381 A | 4/2010 |
| WO | 2010-013378 A1 | 2/2010 |

* cited by examiner

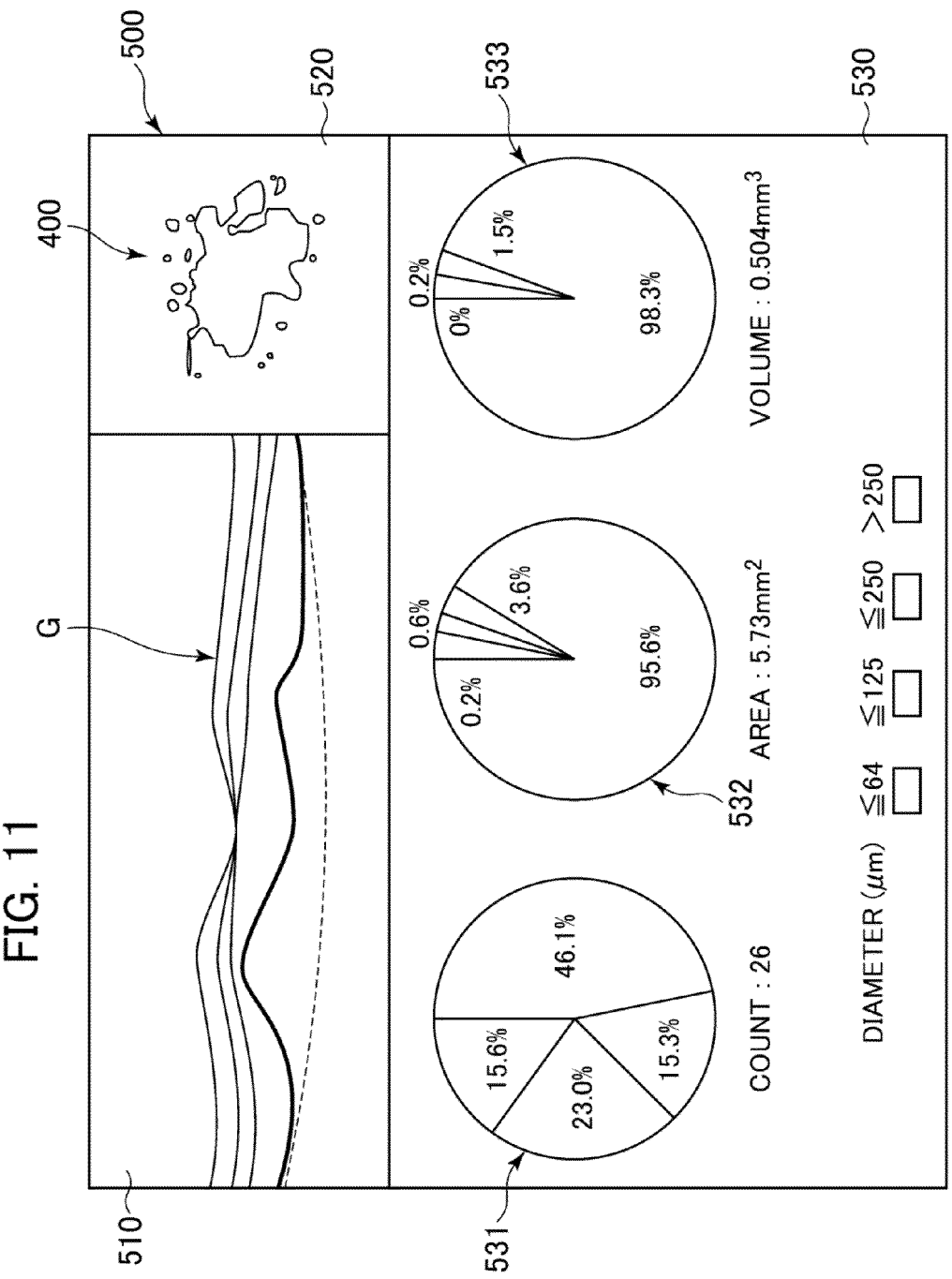

FUNDUS ANALYZING APPARTUS AND FUNDUS ANALYZING METHOD

TECHNICAL FIELD

The present invention relates to a technology for analyzing images of a fundus formed by using optical coherence tomography (OCT).

BACKGROUND ART

In recent years, OCT that forms images of the surface morphology and internal morphology of an object by using a light beam from a laser light source or the like has attracted attention. Unlike an X-ray CT apparatus, OCT is noninvasive to human bodies, and is therefore expected to be utilized in the medical field and biological field. For example, in the ophthalmology, apparatuses that form images of a fundus and a cornea are in a practical stage.

Patent Document 1 discloses a device to which OCT is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Patent Document 1 uses a technique of so-called "Fourier Domain OCT." That is to say, the device irradiates a low coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the device described in Patent Document 1 is provided with a Galvano mirror that scans with a light beam (a signal light), and is thereby configured to form an image of a desired measurement target region of the object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction (x-direction) and the vertical direction (y-direction) to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Patent Documents 3 and 4 disclose other types of OCT devices. Patent Document 3 describes an OCT device that images the morphology of an object by sweeping the wavelength of light that is irradiated to an object, acquiring the spectral intensity distribution based on an interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses a configuration obtained by applying OCT in the ophthalmic field. The device described in this document includes a function that captures an image of a fundus to form a fundus image, and a function that measures the fundus using OCT to form tomographic images and three-dimensional images (collectively referred to as "OCT images"). Furthermore, this device analyzes tomographic images and identifies image regions corresponding to layer structures configuring the fundus. The layer structures subject to identification include the inner limiting membrane, the nerve fiber layer, the ganglionic cell lamina, the inner plexiform layer, the inner granular layer, the external plexiform lamina, the external granular layer, the external limiting membrane, the photoreceptor cell layer, and the pigment layer of the retina, etc. Furthermore, because the fundus is configured by layering multiple layer structures, obtaining image regions corresponding to layer structures is equivalent to obtaining image regions corresponding to the boundary positions of adjacent layer structures. Furthermore, from before the use of OCT, retinal cameras have been widely used as devices for observing the fundus (refer to, for example, Patent Document 6).

A device using OCT is advantageous compared to a retinal camera with respect to the fact that it is capable of acquiring high-definition images, and is also capable of acquiring tomographic images and three-dimensional images.

In recent years, there has been growing attention on the ocular disease known as age-related macular degeneration. Age-related macular degeneration is a disorder that occurs due to age-related decreases in function in the macula area of the retina, and causes symptoms such as distortions in visual range, decreases in eyesight, difficulty seeing parts of one's field of view, and an inability to observe a target despite being able to observe surrounding areas normally.

Age-related macular degeneration (exudative) is believed to occur through the following mechanism. Normal retinal cells undergo repeated regeneration. Under normal conditions, waste matter generated during regeneration is dissolved within the retinal pigment epithelium and disappears. However, if the actions of the retinal pigment epithelium decrease due to aging, undissolved waste matter accumulates between the Brusch's membrane and the pigment layer of the retina. When a fundus in this state is imaged, the waste matter is observed as white clusters known as drusen. When the waste matter accumulates, a weak inflammatory response occurs. When this happens, specific chemical substances (chemical mediators) are produced to promote the healing of the inflammation. However, the chemical mediators include agents that promote the generation of blood vessels, and as a result, new blood vessels are generated from the choroid. If the new blood vessels burst through the Brusch's membrane and penetrate to the area below or above the pigment layer of the retina and proliferate, the exudation of blood and blood components becomes acute and decreases in function of the macula become severe.

The presence and distribution of drusen are important factors for diagnosing age-related macular degeneration. Conventionally, fundus images (captured images from a retinal camera) have mainly been used to understand the state of drusen (refer to, for example, Patent Document 7).

PRIOR ART DOCUMENTS

Patent Documents

[Patent Document 1]
Japanese Unexamined Patent Application Publication No. Hei 11-325849
[Patent Document 2]
Japanese Unexamined Patent Application Publication No. 2002-139421
[Patent Document 3]
Japanese Unexamined Patent Application Publication No. 2007-24677
[Patent Document 4]
Japanese Unexamined Patent Application Publication No. 2006-153838
[Patent Document 5]
Japanese Unexamined Patent Application Publication No. 2008-73099
[Patent Document 6]
Japanese Unexamined Patent Application Publication No. Hei 9-276232
[Patent Document 7]
Japanese Unexamined Patent Application Publication No. 2008-295804

DISCLOSURE OF THE INVENTION

Problem that the Invention is to Solve

As described above, drusen is depicted in fundus images as white clusters. Although relatively large drusen can be found in a fundus image based on visual observation and image analysis, relatively small drusen is difficult to discover because the differences in color and brightness compared to surrounding normal regions is small.

Early treatment is important for age-related macular degeneration, but the fact that small drusen cannot be discovered impedes the early discovery of onset. Moreover, if small drusen cannot be discovered, it is not possible to accurately determine how the drusen is actually distributed.

Moreover, if there are traces of laser therapy or retinal detachment in the fundus, it may be difficult to distinguish these from drusen in a fundus image.

The present invention has been devised to resolve the above problems, and the objective of the invention is to provide a fundus analyzing apparatus and a fundus analyzing method capable of effectively detecting drusen.

Means for Solving the Problem

In order to achieve the aforementioned objects, an invention according to claim 1 is a fundus analyzing apparatus comprising: a storage means that stores a plurality of tomographic images that each depict layer structures of a fundus; a layer-region identification means that, based on the pixel values of the pixels of each of said stored tomographic images, identifies the layer region in the tomographic image that corresponds to the pigment layer of the retina; a curve calculation means that, based on the shape of said identified layer region, obtains a convex curve in the direction of depth of said fundus; a protrusion-region identification means that, based on said identified layer region and said obtained curve, identifies protrusion regions where said layer region protrudes in the opposite direction from said direction of depth; and a morphological-information generation means that generates morphological information representing the morphology of the identified protrusion regions.

Further, an invention according to claim 2 is the fundus analyzing apparatus according to claim 1, wherein said curve calculation means includes a characteristic-region identification means that identifies a plurality of characteristic regions within said layer region based on the shape of the layer region identified by said layer-region identification means, and obtains said curve based on the identified plurality of characteristic regions.

Further, an invention according to claim 3 is the fundus analyzing apparatus according to claim 2, wherein said characteristic-region identification means identifies the deepest region in said layer region in said direction of depth based on the shape of said layer region and defines it as said characteristic region, obtains a straight line that passes through said deepest region and comes into contact with said layer region, and defines points of contact between said layer region and said straight line as said characteristic regions.

Further, an invention according to claim 4 is the fundus analyzing apparatus according to claim 3, wherein said characteristic-region identification means sequentially identifies said points of contact by rotating the straight line passing through said deepest region while keeping said deepest region in the center.

Further, an invention according to claim 5 is the fundus analyzing apparatus according to claim 3, wherein said characteristic-region identification means rotates the straight line passing through said deepest region while keeping said deepest region in the center to identify points of contact, and rotates a straight line passing through the identified points of contact while keeping this point of contact in the center to identify more points of contact.

Further, an invention according to claim 6 is the fundus analyzing apparatus according to claim 2, wherein said curve calculation means obtains a quadratic curve based on said identified plurality of characteristic regions as said curve.

Further, an invention according to claim 7 is the fundus analyzing apparatus according to claim 6, wherein said curve calculation means obtains, through the least-squares method, the quadratic curve with the smallest difference with a broken line connecting said plurality of characteristic regions.

Further, an invention according to claim 8 is the fundus analyzing apparatus according to claim 6, wherein said curve calculation means substitutes the respective coordinate values of said plurality of characteristic regions in a coordinate system that has been preliminarily set in said tomographic image into the formula of the quadratic curve and performs a calculation to obtain the coefficient of said formula.

Further, an invention according to claim 9 is the fundus analyzing apparatus according to claim 1, wherein said protrusion-region identification means identifies image regions where the distance in said direction of depth between said layer region and said curve becomes equal to or greater than a prescribed threshold value as said protrusion regions.

Further, an invention according to claim 10 is the fundus analyzing apparatus according to claim 9, wherein said protrusion-region identification means calculates the distance in said direction of depth between each point on said curve and said layer region, determines whether the calculated distances are equal to or greater than said prescribed threshold value, and identifies image regions located between a set of the points on said curve determined to be equal to or greater than said threshold value and said layer region and defines them as said protrusion regions.

Further, an invention according to claim 11 is the fundus analyzing apparatus according to claim 1, wherein said morphological-information generation means includes: a distribution-image forming means that, based on the protrusion regions identified for each said tomographic image by said protrusion-region identification means, forms a distribution image representing the distribution state of protrusion regions in a plane orthogonal to said direction of depth; and a connected-component identification means that, based on the pixel values of the pixels of the formed distribution image, identifies connected components in the protrusion regions in the distribution image, and said morphological-information generation means generates said morphological information based on the identified connected components.

Further, an invention according to claim 12 is the fundus analyzing apparatus according to claim 11, wherein said morphological-information generation means includes a counting means that counts the number of connected components identified by said connected-component identification means, and generates said morphological information based on the number obtained through said count.

Further, an invention according to claim 13 is the fundus analyzing apparatus according to claim 11, wherein said morphological-information generation means includes a size calculation means that calculates the size of each connected component identified by said connected-component identification means, and generates size distribution information representing the distribution of said calculated sizes and defines it as said morphological information.

Further, an invention according to claim 14 is the fundus analyzing apparatus according to claim 13, wherein said size calculation means calculates the area of each said connected component as said size.

Further, an invention according to claim 15 is the fundus analyzing apparatus according to claim 13, wherein said size calculation means calculates the diameter of each said connected component as said size.

Further, an invention according to claim 16 is the fundus analyzing apparatus according to claim 15, wherein said size calculation means calculates the area of each said connected component, and obtains the diameter of a circle having the calculated area and defines it as the diameter of the connected component.

Further, an invention according to claim 17 is the fundus analyzing apparatus according to claim 13, wherein said size calculation means calculates the volume of each said connected component as said size.

Further, an invention according to claim 18 is the fundus analyzing apparatus according to claim 17, wherein said size calculation means calculates the volume of the connected components by integrating the distance in said direction of depth between said layer region and said curve across each said connected component.

Further, an invention according to claim 19 is the fundus analyzing apparatus according to claim 11, wherein said storage means also stores captured images of said fundus, and said morphological-information generation means forms a composite image of said captured image and said distribution image, and defines it as said morphological information.

Further, an invention according to claim 20 is the fundus analyzing apparatus according to claim 1, further comprising: an optical system that divides low-coherence light into a signal light and a reference light, overlaps said signal light that has passed through the fundus of a subject eye and the reference light that has passed through a reference light path, and generates and detects interference light; and an image forming means that, based on the detection results of said interference light, forms a plurality of tomographic images of said fundus, wherein said storage means stores the plurality of tomographic images formed by said image forming means.

Further, an invention according to claim 21 is the fundus analyzing apparatus according to claim 20, wherein said optical system includes a scanning means that sequentially scans the irradiation positions of said signal light on said fundus along a plurality of scanning lines, and said image forming means forms a tomographic image along each of said plurality of scanning lines based on the detection results of said interference light from said optical system.

Further, an invention according to claim 22 is a fundus analyzing apparatus comprising: a storage means that stores three-dimensional images depicting layer structures of a fundus; a layer-region identification means that, based on the pixel values of the pixels of said stored three-dimensional images, identifies the layer region in said three-dimensional image that corresponds to the pigment layer of the retina; a curved-surface calculation means that, based on the shape of said identified layer region, obtains a convex curved surface in the direction of depth of said fundus; a protrusion-region identification means that, based on said identified layer region and said obtained curved surface, identifies protrusion regions where said layer region protrudes in the opposite direction from said direction of depth; and a morphological-information generation means that generates morphological information representing the morphology of the identified protrusion region.

Further, an invention according to claim 23 is the fundus analyzing apparatus according to claim 22, further comprising: an optical system that divides low-coherence light into a signal light and a reference light, overlaps said signal light that has passed through the fundus of a subject eye and the reference light that has passed through a reference light path, and generates and detects interference light; an image forming means that, based on the detection results of said interference light, forms a plurality of tomographic images of said fundus; and a three-dimensional image forming means that forms three-dimensional images based on said plurality of formed tomographic images, wherein said storage means stores the three-dimensional images formed by said three-dimensional image forming means.

Further, an invention according to claim 24 is the fundus analyzing apparatus according to claim 23, wherein said optical system includes a scanning means that sequentially scans the irradiation positions of said signal light on said fundus along a plurality of scanning lines, and said image forming means forms a tomographic image along each of said plurality of scanning lines based on the detection results of said interference light from said optical system.

Further, an invention according to claim 25 is a fundus analyzing method that analyzes a plurality of tomographic images that each depict layer structures of a fundus, comprising the steps of: for each of said plurality of tomographic images, identifying the layer region in the tomographic image that corresponds to the pigment layer of the retina based on the pixel values of the pixels of the tomographic image; obtaining, based on the shape of said identified layer region, a convex curve in the direction of depth of said fundus; identifying, based on said identified layer region and said obtained curve, protrusion regions where said layer region protrudes in the opposite direction from said direction of depth; and generating morphological information representing the morphology of the identified protrusion regions.

Further, an invention according to claim 26 is a fundus analyzing method that analyzes three-dimensional images depicting layer structures of a fundus, comprising the steps of: identifying, based on the pixel values of the pixels of said three-dimensional image, the layer region in said three-dimensional image that corresponds to the pigment layer of the retina; obtaining, based on the shape of said identified layer region, a convex curved surface in the direction of depth of said fundus; identifying, based on said identified layer region and said obtained curved surface, protrusion regions where said layer region protrudes in the opposite direction from said direction of depth; and generating morphological information representing the morphology of the identified protrusion regions.

Effect of the Invention

According to a first mode of the fundus analyzing apparatus and the fundus analyzing method of the present invention, a configuration is provided in which, for each of multiple tomographic images that each depict the layer structures of a fundus, the layer region corresponding to the pigment layer of the retina is identified based on the pixel values of the pixels of the tomographic image, a convex curve in the direction of depth of the fundus is obtained based on the shape of the layer region, protrusion regions of the layer region are identified based on the layer region and the curve, and morphological information representing the morphology of the protrusion regions is generated, and it is therefore possible to individually determine each protruding part of the pigment layer of the retina that may be drusen, and as a result, it is possible to detect even small drusen. Moreover, because the configuration is one in which protrusion regions that are characteristic of drusen are identified based on a tomographic image, it is possible to effectively detect drusen.

According to a second mode of the fundus analyzing apparatus and the fundus analyzing method of the present invention, a configuration is provided in which the layer region corresponding to the pigment layer of the retina is identified based on the pixel values of the pixels of a three-dimensional image depicting the layer structures of a fundus, a convex curved surface in the direction of depth of the fundus is obtained based on the shape of the layer region, protrusion regions of the layer region are identified based on the layer region and the curved surface, and morphological information representing the morphology of the protrusion regions is generated, and it is therefore possible to individually determine each protruding part in the pigment layer of the retina that may be drusen, and as a result, it is possible to detect even small drusen. Moreover, because the configuration is one in which protrusion regions that are characteristic of drusen are identified based on a three-dimensional image, it is possible to effectively detect drusen.

BRIEF DESCRIPTION OF THE DRAWINGS

FIG. 11 is a schematic view showing an example of an analysis results presentation screen displayed by an embodiment of a fundus analyzing apparatus according to the present invention.

MODE FOR CARRYING OUT THE INVENTION

An example of an embodiment of a fundus analyzing apparatus and a fundus analyzing method according to the present invention will be described in detail with reference to the drawings.

The fundus analyzing apparatus of the present invention may be a computer that analyzes OCT images (tomographic images, three-dimensional images) of a fundus, or may be an OCT device that is able to form tomographic images of a fundus using optical coherence tomography. The latter OCT device includes the former computer. Therefore, in the following, the latter OCT device will be described in particular detail.

The fundus analyzing apparatus that is an OCT device may be of any type as long as it can form OCT images of the fundus of a subject eye. In the following embodiment, the Fourier domain type will be described in particular detail. Furthermore, because the central characteristic of the present invention is the process of analyzing OCT images of a fundus, a similar configuration may be used even for other types of OCT devices such as the swept-source type and the en-face type. A measuring action for forming an OCT image is sometimes referred to as an OCT measurement.

As with the device disclosed in Patent Document 5, the fundus analyzing apparatus described below is capable of acquiring both OCT images of a fundus and fundus images.

[Configuration]

Figure 1:
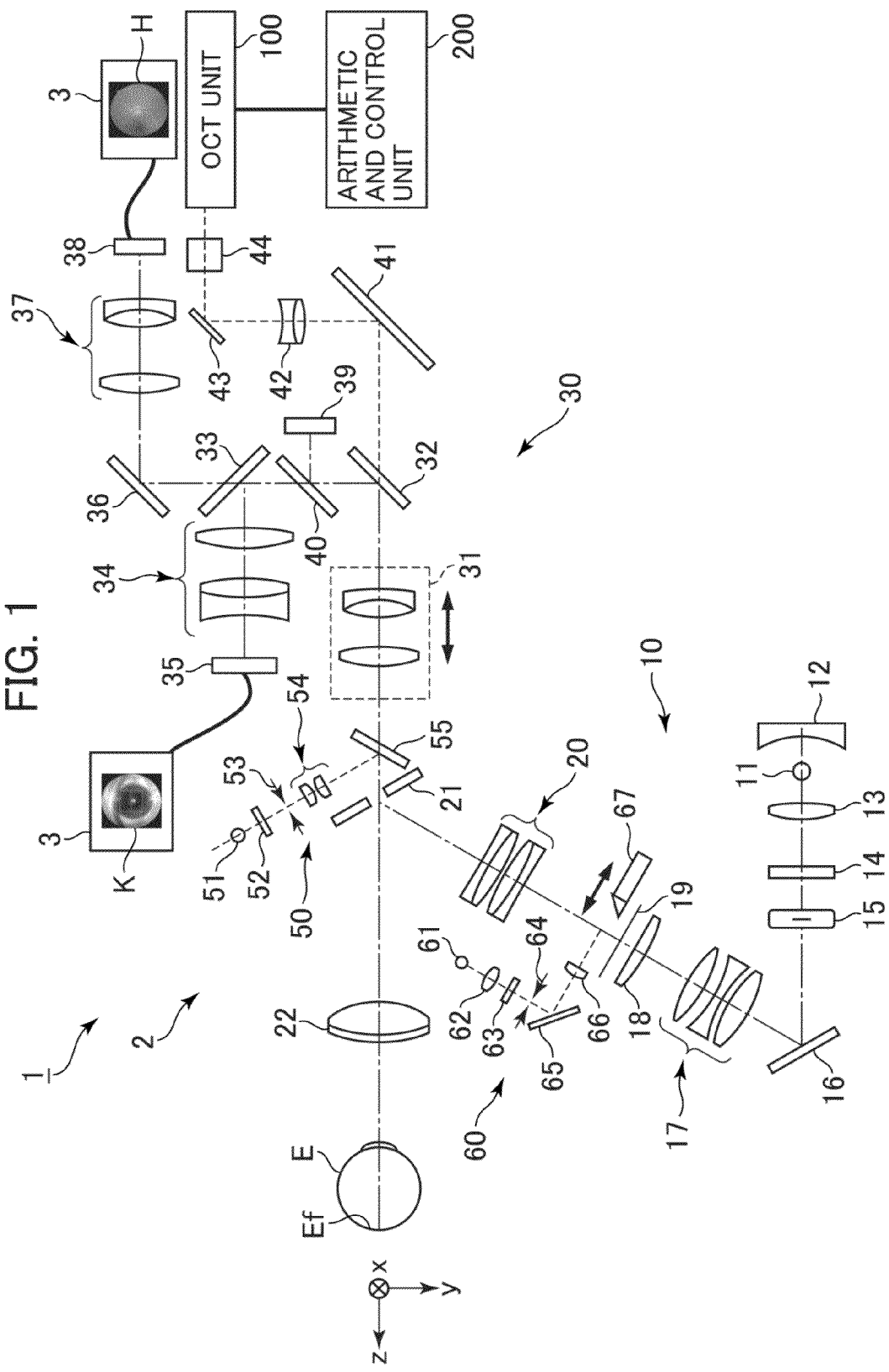
FIG. 1 is a schematic view showing an example of a configuration of an embodiment of a fundus analyzing apparatus according to the present invention.
Figure 2:
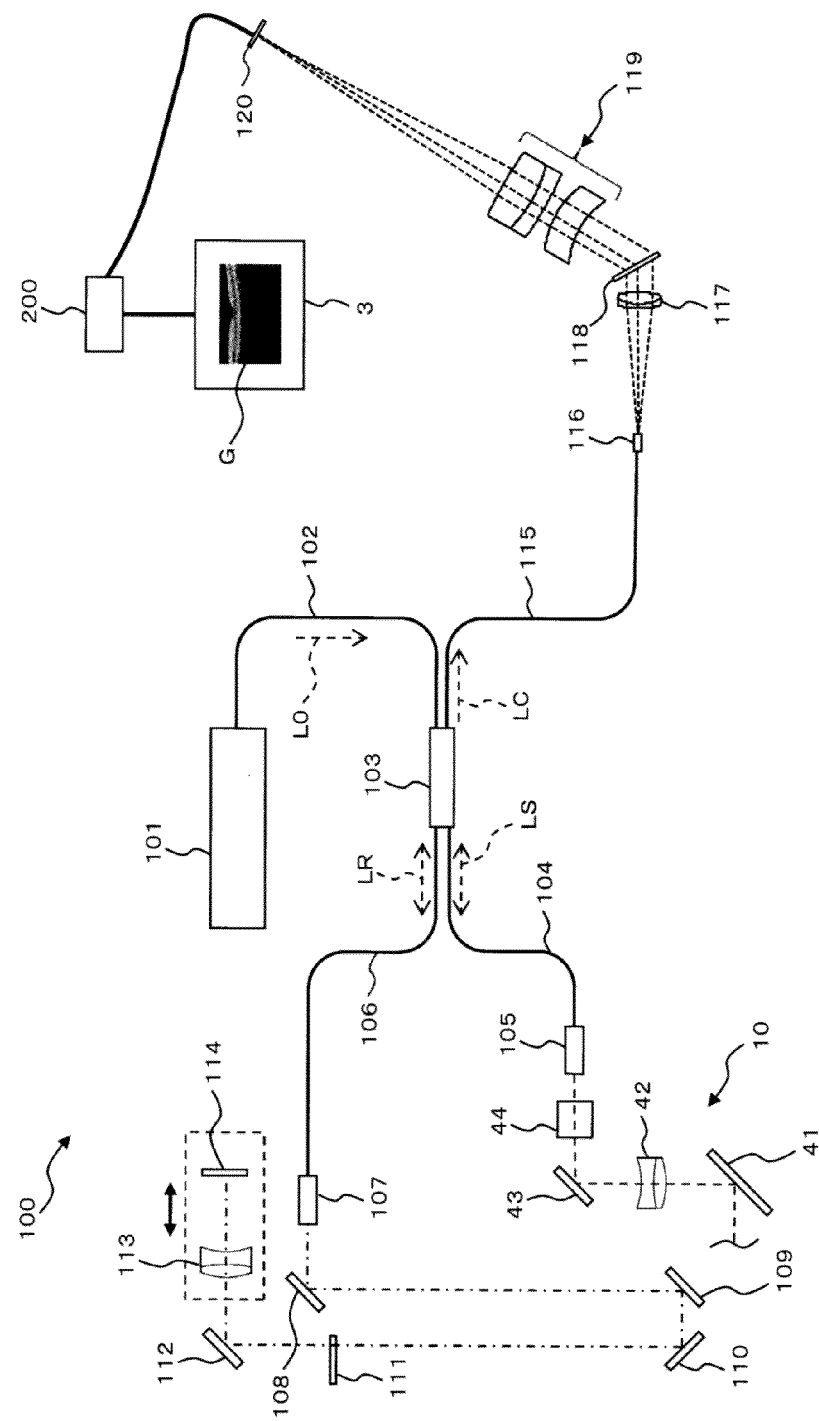
FIG. 2 is a schematic view showing an example of a configuration of an embodiment of a fundus analyzing apparatus according to the present invention.

A fundus analyzing apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for forming a 2-dimensional image (fundus image) representing the surface morphology of the fundus Ef of an eye E. Fundus images include observation images, captured images, etc. The observation image is, for example, a monochrome moving image formed at a prescribed frame rate using near-infrared light. The captured image is, for example, a color image captured by flashing visible light. Furthermore, the retinal camera unit 2 may be configured to be capable of acquiring other types of images such as a fluorescein angiography image, an indocyanine green fluorescent image and a fundus autofluorescent image.

The retinal camera unit 2 is provided with a chin rest and a forehead placement for retaining the face of the subject, similar to a conventional retinal camera. Moreover, like a conventional retinal camera, the retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors 35, 38). Moreover, the imaging optical system 30 guides a signal light coming from the OCT unit 100 to the fundus Ef, and guides the signal light propagated through the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focusing lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image) K based on the fundus reflection light detected by the CCD image sensor 35 is displayed on a display device 3.

The imaging light source 15 consists of, for example, a xenon lamp. The light (imaging illumination light) output from the imaging light source 15 is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (captured image) H based on the fundus reflection light detected by the CCD image sensor 38 is displayed on the display device 3. It should be noted that the display device 3 for displaying an observation image K and the display device 3 for displaying a captured image H may be the same or different.

An LCD (Liquid Crystal Display) 39 displays a fixation target or a visual target for measuring eyesight. The fixation target is a visual target for fixing the eye E, and is used when photographing a fundus or OCT measurement.

Part of the light output from the LCD 39 is reflected by a half-mirror 40, reflected by the dichroic mirror 32, passes through the aperture part of the aperture mirror 21 via the focusing lens 31 as well as a dichroic mirror 55, is refracted by the object lens 22 and projected to the fundus Ef.

By changing a display position of the fixation target on the screen of the LCD 140, it is possible to change a fixation position of the eye E. As the fixation position of the eye E, there are a position for acquiring an image centered on the macula of the fundus Ef, a position for acquiring an image centered on the optic papilla, a position for acquiring an image centered on the fundus center between the macula and the optic papilla, and so on, for example, as in conventional retinal cameras.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from the LED (Light Emitting Diode) 51 of the alignment optical system 50 is reflected by the dichroic mirror 55 via diaphragms 52, 53 and a relay lens 54, passes through the aperture part of the aperture mirror 21, and is projected onto the cornea of the eye E by the object lens 22.

Part of cornea reflection light of the alignment light is transmitted through the dichroic mirror 55 via the object lens 22 and the aperture part, passes through the focusing lens 31, is reflected by the dichroic mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 along with the observation image K. A user conducts alignment by an operation that is the same as conventional retinal cameras. It should be noted that alignment may be performed, by an arithmetic and control unit 200, as a result of analyzing the position of the alignment target and moving the optical system.

In order to conduct focus adjustment, the reflection surface of a reflection rod 67 is provided in a slanted position on the light path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light (split target) captured by the CCD image sensor 35 is displayed on the display device 3 along with an observation image K. The arithmetic and control unit 200, as in the past, analyzes the position of the split target, and moves the focusing lens 31 and the focus optical system 60 for focusing. It should be noted that focusing may be performed manually while visually recognizing the split target.

An optical path including a mirror 41, collimator lens 42, and Galvano mirrors 43, 44 is provided behind the dichroic mirror 32. The optical path is guided to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44.

[OCT Unit]

The OCT unit 100 is provided with an optical system for obtaining a tomographic image of the fundus Ef (see FIG. 2). The optical system has a similar configuration to a conventional Fourier-Domain-type OCT device. That is to say, the optical system is configured to split a low coherence light into a reference light and a signal light, make the signal light propagated through a fundus and the reference light propagated through a reference optical path interfere with each other to generate an interference light, and detects the spectral components of this interference light. This detection result (detection signal) is transmitted to the arithmetic and control unit 200.

The light source unit 101 outputs a broadband, low-coherence light L0. The low-coherence light L0 includes, for example, a near-infrared waveband (approximately 800 nm to 900 nm), and has a temporal coherence length of around several tens of micrometers. Furthermore, a waveband that is not visible to the human eye, such as near-infrared light with a central wavelength of around 1050 to 1060 nm, for example, may be used as the low-coherence light L0.

The light source unit 101 is configured to include light output device, such as an SLD (super luminescent diode), LED, SOA (Semiconductor Optical Amplifier) and the like.

The low coherence light L0 output from the light source unit 101 is guided to a fiber coupler 103 by an optical fiber 102 and split into signal light LS and reference light LR. It should be noted that the fiber coupler 103 acts both as a means to split light (splitter) as well as a means to synthesize light (coupler), but herein the same is conventionally referred to as a "fiber coupler."

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103. Because the irradiation direction (+z direction) of the signal light LS relative to the fundus Ef is the direction from the surface (retinal surface) of the fundus Ef toward the deep portions, this shall be referred to as the direction of depth. Moreover, the direction along the z-axis shall be referred to as the depth direction.

The reference light LR is guided by an optical fiber 106 and becomes a parallel light flux by a collimator lens unit 107. Furthermore, the reference light LR is reflected by mirrors 108, 109, 110, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element for dispersion compensation (pair prism, etc.) and/or an optical element for polarization correction (wave plate, etc.) may also be provided for the optical path (reference optical path) of the reference light LR.

The fiber coupler 103 superposes the fundus reflection light of the signal light LS and the reference light LR reflected by the reference mirror 114. Interference light LC thus generated is guided by an optical fiber 115 and output from an exit end 116. Furthermore, the interference light LC is converted to a parallel light flux by a collimator lens 117, spectrally divided (spectrally decomposed) by a diffraction grating 118, converged by the convergence lens 119, and projected onto the light receiving surface of a CCD image sensor 120. Although the diffraction grating 118 shown in FIG. 2 is of the transmission type, it is possible to use the reflection type.

The CCD image sensor 120 is for example a line sensor, and detects the respective spectral components of the spectrally decomposed interference light LC and converts the components into electric charges. The CCD image sensor 120 accumulates these electric charges and generates a detection signal. Furthermore, the CCD image sensor 120 transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals inputted from the CCD image sensor 120, and forms an OCT image of the fundus Ef. An arithmetic process for this is the same as that of a conventional Fourier-Domain-type OCT device. Furthermore, the arithmetic and control unit 200 performs the under-mentioned analytical process on OCT images of the fundus Ef. This analyticcal process is the characteristics of the present embodiment.

Further, the arithmetic and control unit 200 controls each part of the retinal camera unit 2, the display device 3 and the OCT unit 100. For example, the arithmetic and control unit 200 causes the display device 3 to display a tomographic image G of the fundus Ef (see FIG. 2).

Moreover, as control of the retinal camera unit 2, the arithmetic and control unit 200 executes: control of action of the observation light source 101, the imaging light source 103 and LED's 51 and 61; control of action of the LCD 39; control of movement of the focusing lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; and so on.

The arithmetic and control unit 200 includes a microprocessor, a RAM, a ROM, a hard disk drive, a communication interface, and so on, as in conventional computers. The storage device such as the hard disk drive stores a computer program for controlling the fundus analyzing apparatus 1. The arithmetic and control unit 200 may be provided with a circuit board dedicated for forming OCT images based on detection signals from the CCD image sensor 120. Moreover, the arithmetic and control unit 200 may be provided with operation devices (input devices) such as a keyboard and a mouse, and/or display devices such as LCD.

The retinal camera unit 2, display device 3, OCT unit 100, and arithmetic and control unit 200 may be integrally configured (that is, within a single case), or configured as separate bodies.

[Control System]

Figure 3:
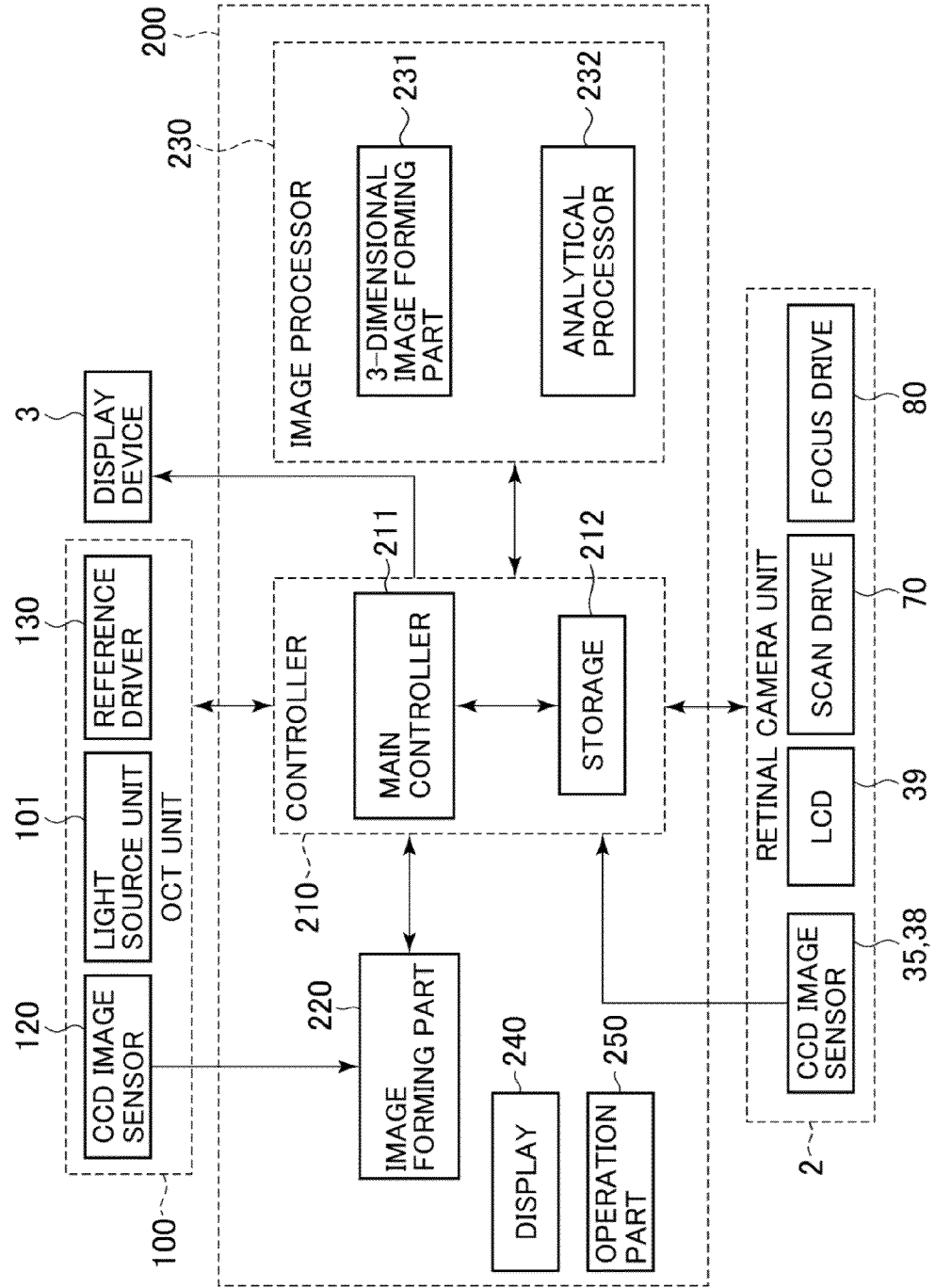
FIG. 3 is a schematic block diagram showing an example of a configuration of an embodiment of a fundus analyzing apparatus according to the present invention.
Figure 4:
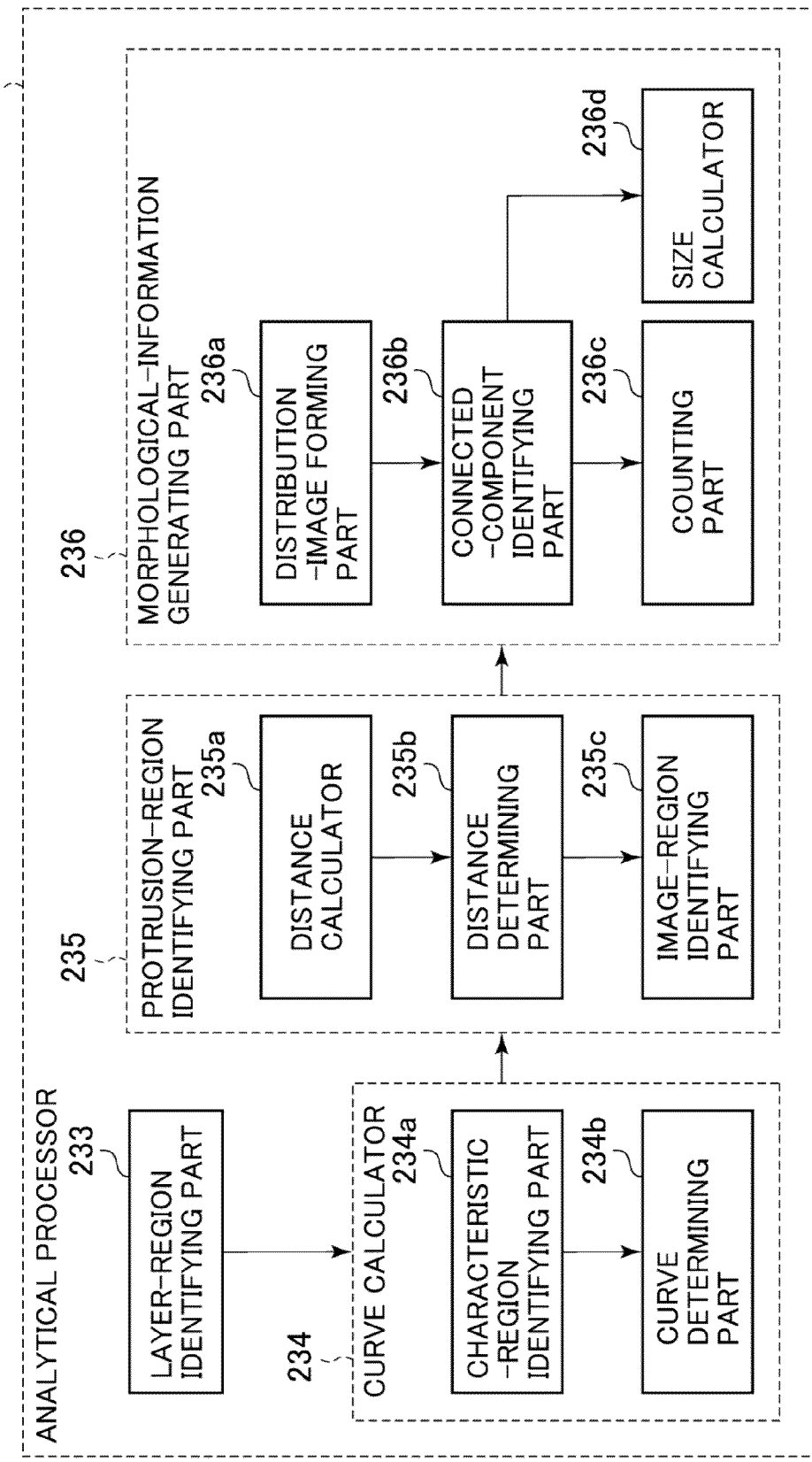
FIG. 4 is a schematic block diagram showing an example of a configuration of an embodiment of a fundus analyzing apparatus according to the present invention.

A configuration of a control system of the fundus analyzing apparatus 1 will be described with reference to FIG. 3 and FIG. 4.

(Controller)

The control system of the fundus analyzing apparatus 1 has a configuration centered on a controller 210 of the arithmetic and control unit 200. The controller 210 includes, for example, the aforementioned microprocessor, RAM, ROM, hard disk drive, and communication interface.

The controller 210 is provided with a main controller 211 and storage 212. The main controller 211 performs the aforementioned various kinds of control. Specifically, the main controller 211 controls a scan driver 70 and a focus driver 80 of the retinal camera unit 2, and further controls the light source unit 101 and a reference driver 130 of the OCT unit 100.

The scan driver 70 is configured, for example, including a servo motor and independently changes the facing direction of the Galvano mirrors 43 and 44. The scan driver 70 consists of one example of the "scanning means" in the invention along with the Galvano mirrors 43 and 44.

The focus driver 80 is configured, for example, including a pulse motor and moves the focusing lens 31 in the optical axis direction. Thereby, the focus position of light towards the fundus Ef is changed.

The reference driver 130 is configured, for example, including a pulse motor and integrally moves the collimator lens 113 as well as the reference mirror 114 along the travelling direction of the reference light LR.

The main controller 211 executes a process of writing data into the storage 212, and a process of reading out the data from the storage 212.

The storage 212 stores various kinds of data. The data stored in the storage 212 is, for example, image data of OCT images, image data of fundus images (observation images, captured images), and eye information. The eye information includes information on the eye, for example, information on a subject such as a patient ID and a name, information on identification of left eye or right eye, and so on. The storage 212 is an example of "storage means" of the present invention.

(Image Forming Part)

An image forming part 220 forms image data of a tomographic image of the fundus Ef based on the detection signals from the CCD image sensor 120. Like the conventional Fourier-Domain OCT, this process includes processes such as noise elimination (noise reduction), filtering, and FFT (Fast Fourier Transform).

The image forming part 220 includes, for example, the aforementioned circuit board and communication interface. It should be noted that "image data" and the "image" presented based on the image data may be identified with each other in this specification. The image forming part 220 is an example of the "image forming means" of the invention.

(Image Processor)

An image processor 230 executes various image processing and analysis on images formed by the image forming part 220. For example, the image processor 230 executes various correction processes such as luminance correction and dispersion correction of images. The image processor 230 includes, for example, the aforementioned microprocessor, RAM, ROM, hard disk drive, circuit board, and so on. The image processor 230 is provided with the three-dimensional image forming part 231 and the analytical processor 232.

(Three-dimensional Image Forming Part)

The three-dimensional image forming part 231 executes known image processes such as an interpolation process of interpolating pixels between tomographic images formed by the image forming part 220, thereby forming image data of a three-dimensional image of the fundus Ef. The three-dimensional image forming part 231 is an example of "three-dimensional image forming means" of the invention.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a three-dimensional coordinate system (namely, embedding into a three-dimensional space).

Based on image data of a three-dimensional image, the image processor 230 is able to form a tomographic image of any cross-section. This process is executed by, for example, identifying pixels (voxels, etc.) positioned on a manually or automatically designated cross-section, arranging the identified pixels in a two-dimensional array, and forming image data representing the morphology of the fundus Ef in the cross-section. As a result of this type of process, it becomes possible to acquire not only a cross-section (the position of the scanning line of the signal light LS) of the original tomographic image but also a tomographic image along a desired cross-section.

(Analytical Processor)

Based on an OCT image of the fundus Ef, the analytical processor 232 executes various analytical processes for determining the morphology and functional state of the fundus Ef. OCT images subject to analysis include tomographic images and three-dimensional images of the fundus Ef. In the present embodiment, OCT images of the macula and its surrounding areas in the fundus Ef in particular are subject to analysis. An example configuration of the analytical processor 232 is shown in FIG. 4. The analytical processor 232 is provided with a layer-region identifying part 233, a curve calculator 234, a protrusion-region identifying part 235, and a morphological-information generating part 236.

(Layer-region Identifying Part)

Based on the pixel values of the pixels of an OCT image subject to analysis, the layer-region identifying part 233 identifies an image region (layer region) in the OCT image that corresponds to the pigment layer of the retina in the fundus Ef.

The layer-region identifying part 233 identifies the layer region by executing a process similar to that of Patent Document 5, for example. This process will be described briefly. The layer-region identifying part 233 first performs preprocessing such as a grayscale conversion process, an image enhancement process, a threshold value process, a contrast conversion process, a binarization process, and edge detection process, an image averaging process, an image smoothing process, a filtering process, etc. on the OCT image, and makes the layer region in the OCT image clear.

Next, the layer-region identifying part 233 analyzes the pixel values (e.g., luminance values) of the pixels configuring the preprocessed OCT image one row at a time along the depth direction (z-axis direction) of the fundus Ef, and identifies pixels corresponding to the boundary positions of adjacent layers. At this time, it is possible to identify pixels corresponding to the boundary positions of the layers by using a filter that spreads in only the depth direction (e.g., a differential filter). Furthermore, it is also possible to perform edge detection of the pixels by using an area filter that spreads in both the depth direction and the direction orthogonal thereto.

As a result of such a process, the layer-region identifying part 233 identifies image regions corresponding to several layers of the fundus Ef. Furthermore, from among the several identified image regions, the layer-region identifying part 233 identifies those that correspond to the pigment layer of the retina. This process will now be described. In the OCT image, the question of which bright layer counting from the retinal surface corresponds to the pigment layer of the retina is already known based on the numerous clinically acquired OCT images of fundi. Consequently, for the OCT image subject to analysis, the retinal surface is first identified, the number of bright layers is counted from the retinal surface side, and the layer corresponding to a prescribed count number is the target layer region.

As another method of identifying the layer regions, the layer regions of the OCT image subject to analysis may be identified based on a standard distance from the retinal surface in the direction of depth toward the pigment layer of the retina. Moreover, in the OCT image, because there are differences in the brightness of each layer of the fundus Ef, it is possible to identify the layer regions by taking these differences into consideration. For example, if the pigment layer of the retina is the Nth layer that is depicted brightly among the layers depicted brightly, it is possible to identify the Nth bright image region from among image resions corresponding to layers identified in the OCT image subject to analysis and define it as a layer region. Furthermore, the method of identifying layer regions is not limited to those described here, and any method may be used as long as the target layer region can be identified.

Furthermore, the OCT images subject to analysis are tomographic images or three-dimensional images. If analyzing a tomographic image, the layer region is identified as an image region with a substantially curved shape (when ignoring the thickness of the layer region). On the other hand, if analyzing a three-dimensional image, the layer region is identified as an image region shaped substantially like curved surfaces (when ignoring the thickness of the layer region). Here, cases of analyzing a tomographic image will be described in detail. Cases of analyzing a three-dimensional will be described later as a variation.

The layer-region identifying part 233 generates information on the identified layer region, such as position information (coordinate values) of the layer region in the OCT image. Furthermore, the layer region may be extracted from the OCT image. Moreover, image information representing the shape of the identified layer region (e.g., a wire model, etc.) may be generated. In any case, the layer-region identifying part 233 should at least identify the layer region corresponding to the pigment layer in the retina in the OCT image.

(Curve Calculator)

The identification results of a layer region (image region with a substantially curved shape) in a tomographic image of the fundus Ef are input into the curve calculator 234. Based on the shape of the layer region, the curve calculator 234 obtains a convex curve ("standard curve") in the direction of depth of the fundus Ef. This standard curve represents the shape of the pigment layer of the retina in a hypothetical case defined based on the shape of the layer region in which there is no drusen on the cross-section. The curve calculator 234 is one example of the "curve calculation means" of the present invention.

If there is no drusen on the cross-section, the layer region is depicted in the tomographic image as a convex curve in the derection of depth. If there is drusen in the cross-section, irregularities corresponding to the drusen are depicted on the identified layer region. The standard curve represents the global shape of a layer region in which these types of irregularities are ignored. To obtain this type of standard curve, the curve calculator 234 is provided with a characteristic-region identifying part 234*a* and a curve determining part 234*b*. The characteristic-region identifying part 234*a* is one example of the "characteristic-region identification means" of the present invention.

(Characteristic-region Identifying Part)

Figure 5A:
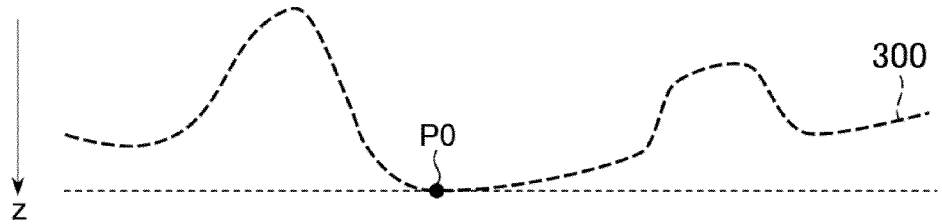
FIG. 5A is a schematic view for explaining an example of processings executed by an embodiment of a fundus analyzing apparatus according to the present invention.
Figure 5B:
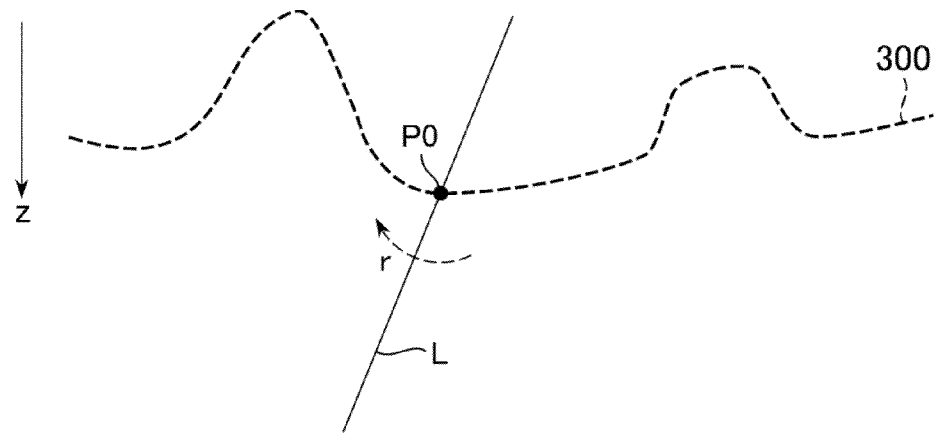
FIG. 5B is a schematic view for explaining an example of processings executed by an embodiment of a fundus analyzing apparatus according to the present invention.
Figure 5C:
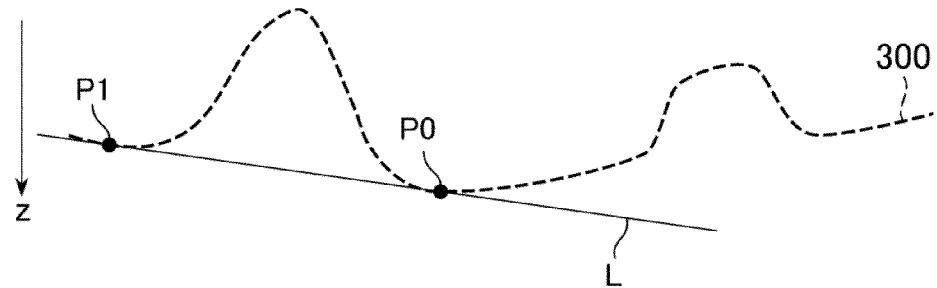
FIG. 5C is a schematic view for explaining an example of processings executed by an embodiment of a fundus analyzing apparatus according to the present invention.

Based on the pixel values of the pixels in the identified layer region, the characteristic-region identifying part 234*a* identifies multiple characteristic regions based on the shape of the layer region. An example of this process is shown in FIG. 5A-5C. Furthermore, FIG. 5A-5C shows part of a layer region identified from a tomographic image.

First, as shown in FIG. 5A, based on the shape of the layer region 300, the characteristic-region identifying part 234*a* identifies the deepest region P0 in the layer region 300 in the direction of depth (+z direction). This process may be executed by, for example, referring to the coordinate values of each pixel in the layer region 300, and identifying the pixel with the greatest z-coordinate values and setting it as the deepest region P0. As another method, in the tomographic image subject to analysis, a straight line orthogonal to the direction of depth may be shifted from the +z direction to the −z direction to set the position in the layer region that first comes into contact with this straight line as the deepest region. The deepest region P0 that is identified in this way is defined as a characteristic region of the layer region 300.

Next, the characteristic-region identifying part 234*a* obtains a straight line that passes through the deepest region P0 and also comes into contact with the layer region 300, and defines the points of contact between the straight line and the layer region 300 as characteristic regions. A specific example of this process will be described. As shown in FIG. 5B, the straight line L that passes through the deepest region P0 is rotated while keeping the deepest region P0 as the center of rotation. FIG. 5B shows a case in which the straight line L is rotated in a clockwise direction.

By rotating the straight line L in this way, as shown in FIG. 5C, at some stage, the straight line L comes into contact with the layer region 300. At this time, the straight line L corresponds to the above "straight line that passes through the deepest region P0 and also comes into contact with the layer region 300". This point of contact P1 is defined as a characteristic region of the layer region 300. Furthermore, because all of the other characteristic regions are positioned more toward −z than the deepest region P0, it is sufficient to rotate the straight line L from a position that passes through the deepest region P0 and is orthogonal to the z-coordinate axis, for example. Moreover, by rotating the straight line L in the opposite (counterclockwise) direction, it is possible to identify characteristic regions positioned on the opposite side to the characteristic region P1 in relation to the deepest region P0.

By repeating this type of process, multiple characteristic regions Pj (j=0, 1, 2 . . . , J) of the layer region 300 are identified. Furthermore, methods of repeating the above process include, for example, the following two methods. Of course, it is also possible to identify the multiple characteristic regions Pj using another method.

As a first repeating method, it is possible to take into consideration the straight line L that always passes through the deepest region P0, and sequentially identify points of contact between the straight line L and the layer region 300. In this case, the points of contact (characteristic regions) are sequentially identified in the manner of a first point of contact, a second point of contact, a third point of contact, etc. as the straight line L is rotated.

As a second repeating method, it is possible to sequentially change the rotational center of the straight line L. Specifically, first, the first point of contact is identified by rotating the straight line L while keeping the deepest region P0 in the center. Next, while keeping the first point of contact in the center, the straight line L is rotated in a similar manner to identify the second point of contact. Next, while keeping this second point of contact in the center, the straight line L is rotated in a similar manner to identify the third point of contact. In this way, multiple points of contact (characteristic regions) are sequentially identified.

Any number of characteristic regions may be identified in the manner described above, but the precision of the following process improves if the number is greater. On the other hand, if the number of identified characteristic regions increases, the resources required for processing increase.
(Curve Determining Part)

The curve determining part 234b determines a standard curve based on the multiple characteristic regions Pj identified by the characteristic-region identifying part 234a. An example of a process executed by the curve determining part 234b is shown in FIG. 6A-6C.

Figure 6A:
FIG. 6A is a schematic view for explaining an example of processings executed by an embodiment of a fundus analyzing apparatus according to the present invention.
Figure 6B:
FIG. 6B is a schematic view for explaining an example of processings executed by an embodiment of a fundus analyzing apparatus according to the present invention.
Figure 6C:
FIG. 6C is a schematic view for explaining an example of processings executed by an embodiment of a fundus analyzing apparatus according to the present invention.

First, the curve determining part 234b connects adjacent ones of the multiple characteristic regions Pj to form a broken line 310 such as that shown in FIG. 6A. Next, using the least-squares method, the curve determining part 234b obtains the quadratic curve in which the difference with the broken line 310 is smallest. This "difference" is, for example, the area of the region located between the broken line 310 and the quadratic curve. As a result, an approximate quadratic curve 320 to the broken line 310 such as that shown in FIG. 6B is obtained. FIG. 6C shows the positional relationship between the quadratic curve 320 and the layer region 300. This quadratic curve 320 is the standard curve. As described above, because the OCT image (tomographic image) subject to analysis is obtained by measuring the macula and its surrounding regions, the standard curve is convex in the direction of depth.

As another example of a method of determining the standard curve, it is possible to change the coefficient parameters of the quadratic curve to form a family of curves, and obtain the quadratic curve in this family of curves that most closely matches the shape of the broken line 310 through pattern matching, etc.

As another example, a method that does not take into consideration the broken line 310 and is based on the coordinate values of the characteristic regions Pj is described. First, the coordinate values of multiple characteristic regions Pj are substituted into the equation of the quadratic curve to form simultaneous equations, and the target quadratic curve is obtained by solving these simultaneous equations and calculating the undetermined coefficients. When applying this example, the number of characteristic regions (e.g., 6) should be at least the number of undetermined coefficients in the quadratic curve. Furthermore, it is also possible to take into consideration the characteristics (e.g., whether it is convex downward, or parity, etc.) of the standard curve to decrease the number of undetermined coefficients and thereby reduce the required number of characteristic regions.
(Protrusion-region Identifying Part)

Based on the layer regions identified by the layer-region identifying part 233 and the standard curve obtained by the curve calculator 234, the protrusion-region identifying part 235 identifies image regions (protrusion regions) where the layer region protrudes in the opposite direction (−z direction) from the direction of depth. The protrusion-region identifying part 235 is one example of the "protrusion-region identification means" of the present invention.

Furthermore, it is also possible to identify the entire image region that protrudes in the −z direction relative to the standard curve as a protrusion region, but in the present embodiment, to circumvent natural irregularities and noise, etc. in the pigment layer of the retina, only parts that protrude by at least a prescribed distance from the standard curve are detected, and in this way, the precision of identification of protrusion regions is improved. For this reason, the protrusion-region identifying part 235 is provided with a distance calculator 235a, a distance determining part 235b, and an image-region identifying part 235c.
(Distance Calculator)

The distance calculator 235a calculates the distance in the direction of depth between each point on the standard curve and the layer region. This process does not need to be executed for all points (pixels) on the standard curve, and may be performed at a prescribed pixel interval (e.g., every 5 pixels). The distance calculating process may be performed by, for example, counting the number of pixels between a point (pixel) on the standard curve and a corresponding point (pixel) on the layer region, and calculating the interval between adjacent pixels based on a unit distance and the count results. Moreover, the interval may be obtained based on the measuring magnification of the image and the distance in the image between pixels subject to distance measurement. Furthermore, the distance calculated by the distance calculator 235a may be a conversion of the distance in the image (distance defined by the xyz coordinate system, or pixel interval) into a distance in real-space, or the distance in the image as it is may be used.
(Distance Determining Part)

The distance determining part 235b determines whether each distance calculated by the distance calculator 235a is equal to or greater than a prescribed threshold value. This threshold value is set in advance, for example, based on many clinical examples. Moreover, it is also possible to set the threshold value by taking into consideration the measuring accuracy, etc. of the device.

The distance determining part 235b assigns identification information (e.g., a flag or a tag) to points (pixels) on the standard curve where the distance is determined to be equal to or greater than the prescribed threshold value.

(Image-region Identifying Part)

The image-region identifying part 235c identifies image regions located between a set of pixels on the standard curve that have been assigned identification information by the distance determining part 235b (i.e., a set of points on the standard curve where the distance is determined to be equal to or greater than the prescribed threshold value) and the layer region, and defines the image regions as target protrusion regions.

Figure 7:
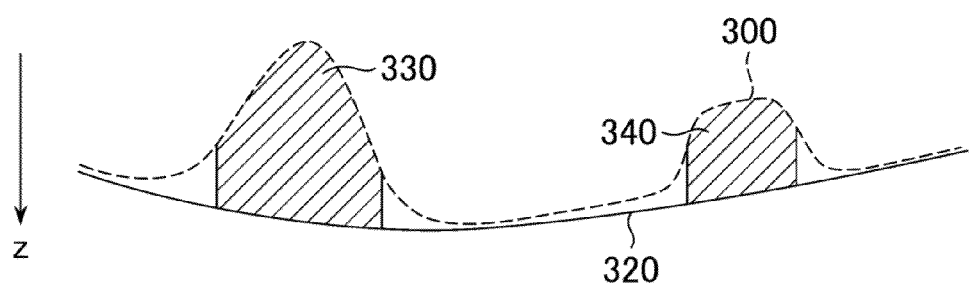
FIG. 7 is a schematic view for explaining an example of processings executed by an embodiment of a fundus analyzing apparatus according to the present invention.

An example of protrusion regions identified in this manner is shown in FIG. 7. The protrusion regions 330, 340 are each image regions located between the layer region 300 and the standard curve 320, and are partial regions where the distance between the layer region 300 and the standard curve 320 is equal to or greater than the prescribed threshold value. As shown in FIG. 7, from among the layer region 300 that protrudes in the −z direction relative to the standard curve 320, its base part (the part where the distance is less than the prescribed threshold value) is not included in the protrusion regions 330, 340.

(Morphological-information Generating Part)

The morphological-information generating part 236 generates information (morphological information) representing the morphology of the identified protrusion regions. The morphology of the protrusion regions includes quantity, size, and distribution state, etc. The morphological-information generating part 236 is an example of the "morphological-information generation means" of the present invention. The morphological-information generating part 236 is provided with a distribution-image forming part 236a, a connected-component identifying part 236b, a counting part 236c, and a size calculator 236d.

(Distribution-image Forming Part)

If protrusion regions are identified for each of multiple tomographic images by the protrusion-region identifying part 235, the distribution-image forming part 236a forms distributions images representing the distribution states of the protrusion regions in the xy plane that is orthogonal to the direction of depth. The distribution-image forming part 236a is an example of the "distribution-image forming means" of the present invention. The details of the processes executed by the distribution-image forming part 236a are described below.

Multiple tomographic images are obtained by executing, for example, a three-dimensional scan (described below). The three-dimensional scan is a scanning mode in which the irradiation position of the signal light LS is scanned along, for example, multiple straight scanning lines each of which lies in the x-direction as well as which are arranged in the y-direction. As a result of a three-dimensional scan, multiple tomographic images of the cross-sections along each scanning line are obtained.

Based on the protrusion regions identified for each of these tomographic images, the distribution-image forming part 236a forms a distribution image of the protrusion regions in the xy plane. In each tomographic image, each protrusion region is an image region that extends in the x-direction (direction of the scanning line). Moreover, multiple tomographic images are arranged in the y-direction. By setting multiple tomographic images in an array in the y-direction, the protrusion regions in each tomographic image are combined and a two-dimensional distribution (distribution in the xy plane) of the protrusion regions is obtained.

At this time, if the protrusion regions in adjacent tomographic images are adjacent in the y-direction, the pixels between these protrusion regions may be set as a protrusion region. This process is particularly useful if the interval (interval between scanning lines) of the adjacent tomographic images is sufficiently narrow.

The distribution-image forming part 236a forms the distribution image by, for example, expressing the pixel values of pixels corresponding to protrusion regions and other pixels differently. As an example, the protrusion regions and other regions are distinguished and expressed with two values to form a binary image, and this is used as the distribution image.

Figure 8:
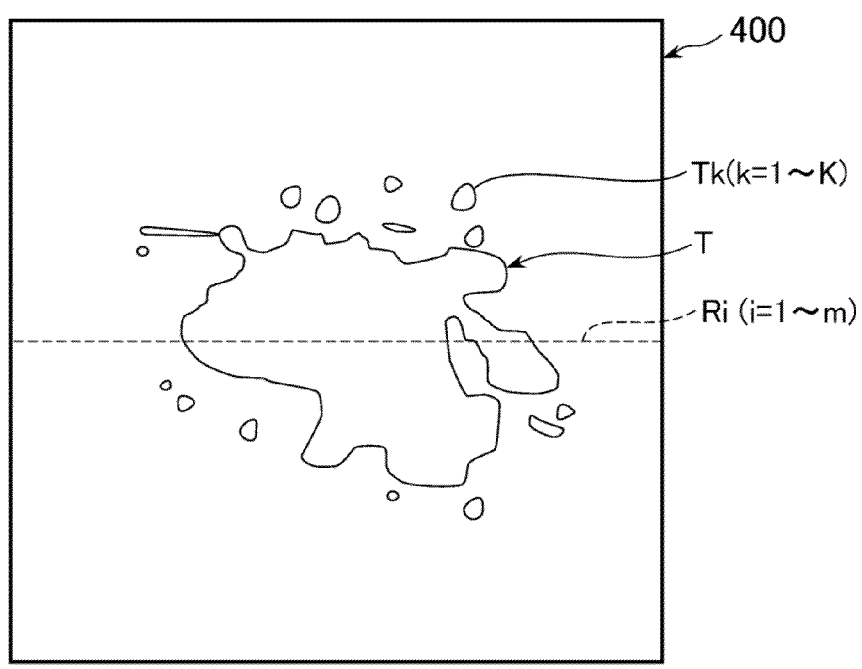
FIG. 8 is a schematic view for explaining an example of processings executed by an embodiment of a fundus analyzing apparatus according to the present invention.

An example of a distribution image formed in this manner is shown in FIG. 8. This distribution image 400 represents the distribution state of the protrusion region T when viewing the fundus Ef from the incoming direction (−z direction) of the signal light LS. The distribution image 400 is formed based on multiple tomographic images using multiple scanning lines Ri (i=1 to m) as cross-sections.

(Connected-component Identifying Part)

Based on the pixel values of the pixels of the distribution image, the connected-component identifying part 236b identifies each connected component of the protrusion regions in the distribution image. Each connected component corresponds to an individual protrusion region. The connected-component identifying part 236b is an example of the "connected-component identification means" of the present invention.

An example of a process executed by the connected-component identifying part 236b will be described with reference to FIG. 9. The distribution image subject to analysis is a binary image, and regions (background images) other than the protrusion regions are, for example, represented with a pixel value (luminance value) of 0. Each square shown in FIG. 9 represents one pixel.

Figure 9A:
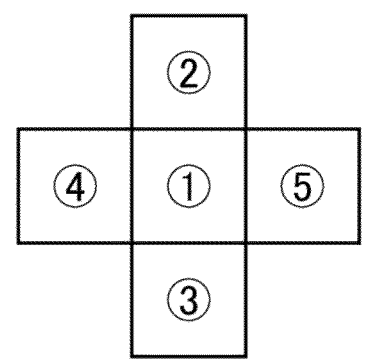
FIG. 9A is a schematic view for explaining an example of processings executed by an embodiment of a fundus analyzing apparatus according to the present invention.

Using the pixel "1" (the "1" in rounded letters) as a standard, as shown in FIG. 9A, the pixels "2", "3", "4", and "5" that are adjacent at the upper, lower, left, and right positions of the pixel "1" (i.e., the +x side, −x side, +y side, and −y side of the pixel "1") and that have the same pixel value as the pixel "1" are each determined to be connected to the pixel "1".

Figure 9B:
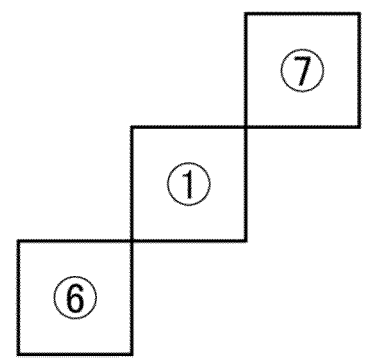
FIG. 9B is a schematic view for explaining an example of processings executed by an embodiment of a fundus analyzing apparatus according to the present invention.

The other pixels (i.e., the pixels that are not adjacent at the upper, lower, left, and right positions of the pixel "1" or the pixels that have a different pixel value from the pixel "1") are determined not to be connected to the pixel "1". For example, as shown in FIG. 9B, the pixels "6" and "7" that are diagonally adjacent to the pixel "1" are determined to be non-connective, even if they have the same pixel value as the pixel "1".

Figure 9C:
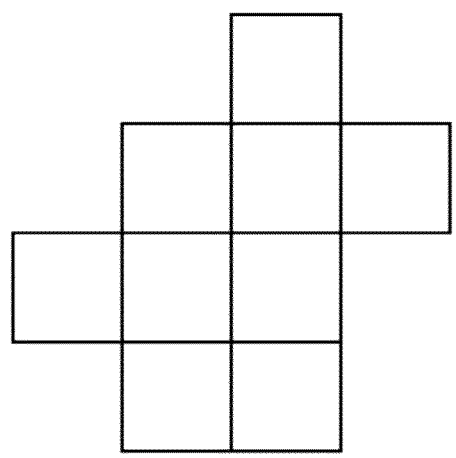
FIG. 9C is a schematic view for explaining an example of processings executed by an embodiment of a fundus analyzing apparatus according to the present invention.

When the connective state of the pixels is determined using this method, the 9 pixels shown in FIG. 9C are determined to be connected. If there are no pixels connected to each of these 9 pixels, the set of these 9 pixels forms one connected component.

The connected-component identifying part 236b obtains each connected component of the protrusion regions in the distribution image based on this type of standard for determining connectivity. For example, based on the distribution image 400 shown in FIG. 8, the connected-component identifying part 236b identifies each connected component Tk (k=1 to K) of the protrusion region T.

Furthermore, the process of identifying connected components can be executed not only for binary images but also for multivalued images. For example, each connected component can be identified by setting a prescribed threshold value and performing a comparison with that threshold value to determine whether a pixel is of a protrusion region or of a background region. Moreover, instead of identifying connected components based on adjacent pixels as described above, it is also possible to identify each connected component by performing, for example, an edge detection process on the distribution image to detect the edges of the protrusion regions.

(Counting Part)

The counting part 236c counts the number of connected components identified by the connected-component identifying part 236b. This process is executed by sequentially assigning the numbers 1, 2, etc. to multiple connected components (sets of pixels) in a prescribed order (e.g., from the top left of the distribution image to the bottom right), and defining the largest assigned number as the number of connected components. The counting part 236c is an example of the "counting means" of the present invention. Furthermore, by performing a labeling process, etc. on the distribution image, the identification process and counting process for the connected components may be performed simultaneously.

(Size Calculator)

The size calculator 236d calculates the size of each connected component identified by the connected-component identifying part 236b. Indices representing the size of the connected components include area, diameter (diameter or radius), and volume, etc. Volume refers to the volume of the protrusion region that is included in the connected component. The size calculator 236d is an example of the "size calculation means" of the present invention. Examples of size calculating processes for the connected components are described below.

First, an example process for obtaining the area of a connected component will be described. Each connected component is a set of multiple pixels determined to be connected. Each pixel has a preliminarily set area (unit area). This unit area may be set arbitrarily for a distribution image or an OCT image. For example, it is possible to take into consideration the measuring magnification and setting the real-space area corresponding to one pixel as the unit area. The size calculator 236d calculates the product of the number of pixels contained in each connected component and the unit area, and defines it as the area of the connected component.

Next, an example process for obtaining the diameter of a connected component will be described. The size calculator 236d first calculates the area as described above. Then, the size calculator 236d defines the diameter (or radius) of a circle having the same area as the diameter of the connected component. Furthermore, it is also possible to retrieve the longest line segment included in the connected component and using the length of this line segment as the diameter of the connected component. In addition, any distance that can characterize the connected component may be used as the diameter.

Next, an example process for obtaining the volume of a connected component will be described. As described above, the distance in the direction of depth between each point on the standard curve and the layer region has already been calculated by the distance calculator 235a. By integrating the distances across each connected component, the size calculator 236d calculates the volume of (the protrusion region included in) this connected component.

Furthermore, the method for calculating size is not limited to those described above. Moreover, the indices (dimensions) representing size are also not limited to those described above.

(Display and Operation Part)

The display 240 is configured including a display device of the aforementioned arithmetic and control unit 200. The operation part 250 is configured including an operation device of the aforementioned arithmetic and control unit 200. Furthermore, the operation part 250 may also include various kinds of buttons or keys provided with the case of the fundus analyzing apparatus 1 or its outside. For example, if the retinal camera unit 2 has a case that is the same as conventional retinal cameras, a joy stick, operation panel, etc. provided with the case may also be included in the operation part 250. Furthermore, the display 240 may also include various display devices such as a touch panel monitor, etc. provided with the case of the retinal camera unit 2.

The display 240 and the operation part 250 do not need to be composed as separate devices. For example, like a touch panel LCD, a device in which the display function and the operation function are integrated can be used.

[Scan with Signal Light and OCT Image]

A scan with the signal light LS and an OCT image will be described.

The scanning patterns of the signal light LS by the fundus analyzing apparatus 1 is, for example, a horizontal scan, vertical scan, cruciform scan, radial scan, circular scan, concentric scan, and helical scan. These scanning patterns are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory while making the turning radius gradually smaller (or greater).

Because the galvano mirrors 43, 44 are configured to scan the signal light LS in mutually perpendicular directions, it is possible to independently scan the signal light LS in the x-direction and the y-direction. Furthermore, by simultaneously controlling the orientations of the galvano mirrors 43, 44, it is possible to scan the signal light LS along any trajectory on the xy plane. As a result, various scanning patterns such as those described above may be realized.

By scanning the signal light LS in the mode described above, it is possible to form tomographic images of a cross-section (xz plane) in the depthwise direction along scanning lines (scan trajectory). Moreover, in a case that the interval between scanning lines is narrow, it is possible to form the aforementioned three-dimensional image.

A region on the fundus Ef subjected to scanning by the signal light LS as above, that is a region of the fundus Ef subject to OCT measurement, is referred to as a scanning region. A scanning region in three-dimensional scanning is a rectangular-shaped region in which multiple horizontal scans are arranged. This scanning region corresponds to the image region of the distribution image 400 shown in FIG. 8. Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

[Operations]

Figure 10:
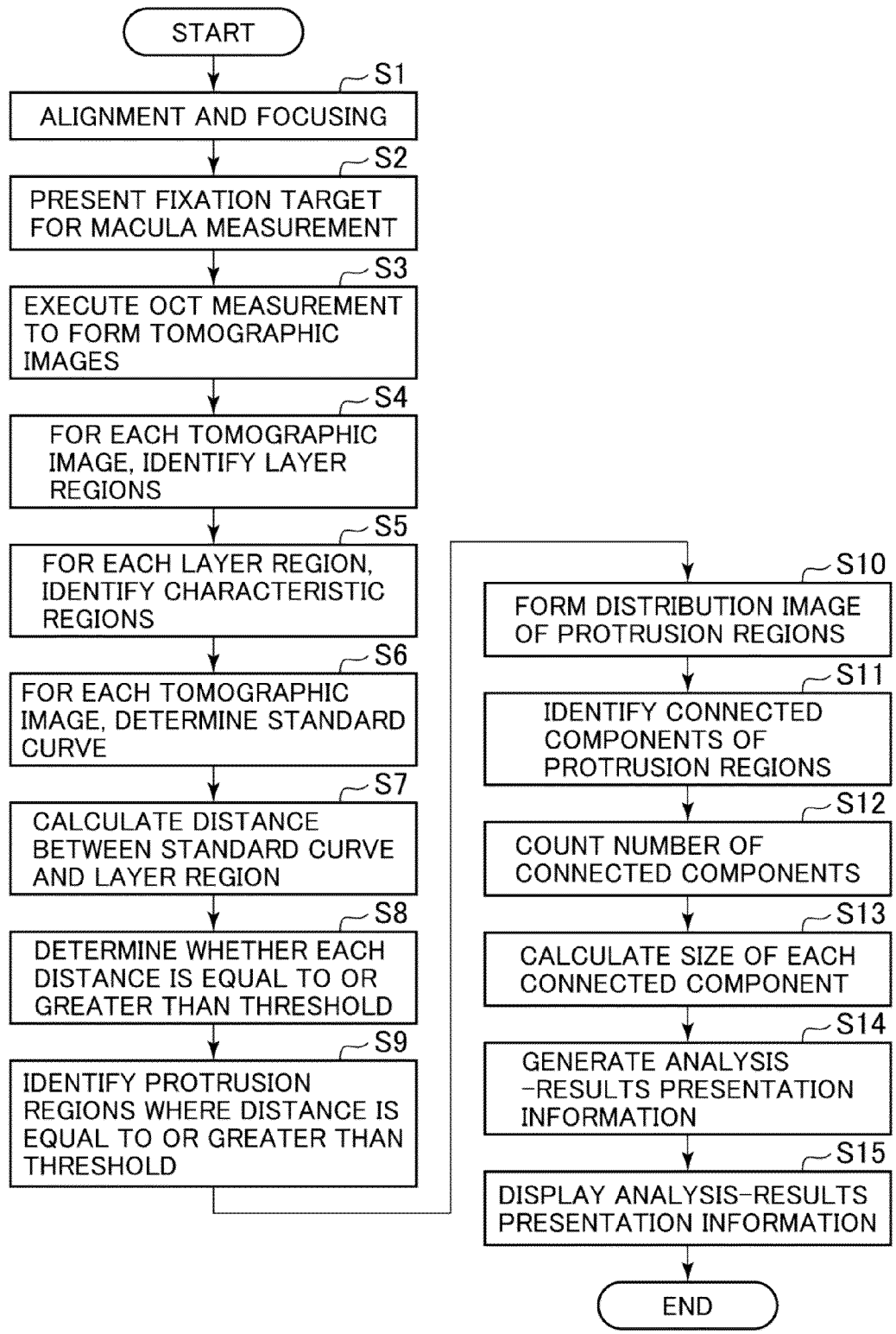
FIG. 10 is a flowchart showing an example of an action of an embodiment of a fundus analyzing apparatus according to the present invention.

Operations of the fundus analyzing apparatus 1 will be described. An operational example of the fundus analyzing apparatus 1 is shown in FIG. 10.

First, alignment and focusing of the subject eye E is performed in a conventional manner (S1). Next, the main controller 211 controls the LCD 39 and presents the subject eye with a fixation target for macula measurement (S2). In this state of fixation, OCT measurement using, for example, a three-dimensional scan is executed, and multiple tomographic images of the macula and the surrounding area of the fundus Ef are formed (S3). The main controller 211 stores these tomographic images in the storage 212.

In response to a start request for analytical processing, for example, the main controller 211 reads out multiple tomographic images from the storage 212 and sends them to the analytical processor 232.

For each tomographic image, the layer-region identifying part 233 identifies the layer region corresponding to the pigment layer of the retina in the fundus Ef based on the pixel values of the pixels (S4). The identification results are sent to the curve calculator 234.

For each tomographic image, based on the pixel values of the pixels in the layer region identified in step 4, the characteristic-region identifying part 234*a* of the curve calculator 234 identifies multiple characteristic regions based on the shape of the layer region (S5). The identification results are sent to the curve determining part 234*b*.

For each tomographic image, based on the multiple characteristic regions identified in step 5, the curve determining part 234*b* determines the standard curve for the layer region (S6). Information on the determined standard curve is sent to the protrusion-region identifying part 235.

For each tomographic image, the distance calculator 235*a* of the protrusion-region identifying part 235 calculates the distance in the direction of depth between each point on the standard curve and the layer region (S7). The calculated results are sent to the distance determining part 235*b*.

For each tomographic image, the distance determining part 235*b* determines whether each calculated result of the distances calculated in step 7 is equal to or greater than a prescribed threshold value (S8). The determination results are sent to the image-region identifying part 235*c*.

For each tomographic image, the image-region identifying part 235*c* identifies image regions located between the sets of the points on the standard curve where the distance has been determined to be equal to or greater than the prescribed threshold value in step 8 and the layer region, and obtains protrusion regions (S9). Information on the obtained protrusion regions is sent to the morphological-information generating part 236.

Based on the protrusion regions in the multiple tomographic images identified in step 9, the distribution-image forming part 236*a* of the morphological-information generating part 236 forms a distribution image representing the distribution state of the protrusion regions in the xy plane that is orthogonal to the direction of depth of the fundus Ef (S10). The formed distribution image is sent to the connected-component identifying part 236*b*.

Based on the pixel values of the pixels of the distribution image formed in step 10, the connected-component identifying part 236*b* identifies connected components of the protrusion regions in the distribution image (S11). The identification results are sent to both the counting part 236*c* and the size calculator 236*d*.

The counting part 236*c* counts the number of connected components identified in step 11 (S12).

The size calculator 236*d* calculates the size of each connected component identified in step 11 (S13). In this operational example, the diameter, area, and volume are calculated as the size of the connected component.

Based on the various information obtained in the above operational example, including the morphological information obtained in steps 12 and 13, the analytical processor 232 generates information for presenting the analysis results (analysis-results presentation information) (S14).

The main controller 211 causes the display 240 to display the analysis results based on the analysis-results presentation information (S15). The analysis results represent the presence or absence of drusen in the fundus Ef, as well as the size and distribution, etc. of drusen present in the fundus Ef. Furthermore, it is also possible to print and output an analysis report based on the analysis-results presentation information. Moreover, it is also possible to transmit the analysis-results presentation information, the information obtained in the above processes, and information related to a patient or a subject eye, etc. to an external device, or to store such information in a storage medium. With the above, the processes of the present operational example are ended.

An example of the screen displayed in step 15 is shown in FIG. 11. On a tomographic image display 510 of an analysis-results display screen 500, one image (representative tomographic image) G is displayed from among the multiple tomographic images formed in step 3. The representative tomographic image G is a tomographic image based on, for example, a scanning line that passes through the central position of the scanning region of a three-dimensional scan. Furthermore, the tomographic image displayed on the tomographic image display 510 is not limited to this.

It is also possible to display a standard curve (shown with broken lines in FIG. 11) on the representative tomographic image G. Moreover, a configuration may be used in which prescribed image regions within the representative tomographic image G, such as the image region corresponding to the fundus surface or the layer region corresponding to the pigment layer of the retina, are clearly indicated. Moreover, it is also possible to clearly indicate protrusion regions in the representative tomographic image G. This process of clear indication involves, for example, changing the luminance, displaying using a prescribed display color, or displaying using a prescribed filling pattern.

On a distribution image display 520, the distribution image 400 formed in step 10 is displayed. The distribution image 400 is a visual depiction of the distribution state of drusen near the macula in the fundus Ef.

Furthermore, if a fundus image (captured image H) of the fundus Ef is acquired, it is possible to display a composite image of the distribution image 400 and the captured image H. This composite image is, for example, one in which the distribution image 400 is superimposed and displayed over the captured image H. Moreover, the composite image may be a single image obtained by synthesizing the captured image H and the distribution image 400. The image alignment process at this time may be performed by matching corresponding characteristic regions (macula, bifurcations of blood vessels, lesioned parts, etc.) in the images. Moreover, it is also possible to integrate the pixel values of the pixels in each tomographic image in the z-direction to form a two-dimensional image, align this two-dimensional image with the captured image H, and align the distribution image and the captured image H based on the results of this alignment.

On an analysis results display 530, the analysis results of protrusion regions that may be drusen are displayed. In this display example, a quantity distribution graph 531, an area distribution graph 532, and a volume distribution graph 533 are displayed. Each of these distributions is obtained by categorizing the identified connected components by size (4 ranges of diameters: 64 µm or less, greater than 64 µm but no greater than 125 µm, greater than 125 µm but no greater than 250 µm, and greater than 250 µm). This categorization process is executed by the analytical processor 232.

The quantity distribution graph 531 represents the distribution of the quantity of the connected components in the protrusion regions counted in step 12. In the lower part of the quantity distribution graph 531, the quantity (count number) of connected components is displayed. The quantity and quantity distribution of the connected components correspond to the quantity and quantity distribution of drusen present near the macula in the fundus Ef.

The area distribution graph 532 represents the distribution of the area of the connected components calculated in step 13. In the lower part of the area distribution graph 532, the mean area of the connected components is displayed. The area and area distribution of the connected components correspond to the area and area distribution of the drusen present near the macula in the fundus Ef. Furthermore, this area represents the area in the xy plane when viewing from the −z direction toward the +z direction.

The volume distribution graph 533 represents the distribution of the volume of the connected components calculated in step 13. In the lower part of the volume distribution graph 533, the mean volume of the connected components is displayed. The volume and volume distribution of the connected components correspond to the volume and volume distribution of drusen present near the macula in the fundus Ef.

[Actions and Effects]

The actions and effects of the fundus analyzing apparatus 1 as described above will be described.

For each of the multiple tomographic images depicting each layer structure of the fundus Ef, the fundus analyzing apparatus 1 operates to identify the layer region corresponding to the pigment layer of the retina based on the pixel values of the pixels in the tomographic image, obtain a standard curve based on the shape of the layer region, identify protrusion regions in the layer region based on the layer region and the standard curve, and generate morphological information representing the morphology of the protrusion regions.

The morphological information is formed by identifying the connected components in the protrusion regions corresponding to individual drusen and obtaining the quantity and size thereof. Moreover, the morphological information may include information representing the distribution of the quantity and size of the connected components (drusen) (e.g., the circular graphs 531-533 in FIG. 11). Furthermore, the morphological information may include image information such as a tomographic image depicting protruding configurations and protrusion regions in the layer region, a distribution image representing the distribution of protrusion regions, or a composite image of a captured image of a fundus and the distribution image, etc.

By performing these types of analytical processes on the tomographic images, it is possible to individually determine each protruding part of the pigment layer of the retina that may be drusen. As a result, detection is possible even for small drusen. Moreover, because the configuration is one in which protrusion regions that are characteristic of drusen are identified based on tomographic images, it is possible to effectively detect drusen.

Furthermore, the fundus analyzing apparatus of the present invention may be the entirety of the fundus analyzing apparatus 1 including OCT measurement functions, or may be only the arithmetic and control unit 200 that executes the above analytical processing. In other words, the fundus analyzing apparatus of the present invention may be an OCT device capable of executing the above analytical processing, or may be a computer capable of executing the above analytical processing. This OCT device performs OCT measurement to form tomographic images of a fundus, and performs the above analytical processing on these tomographic images. Furthermore, it is also possible to perform the above analytical processing on tomographic images acquired from an external device. On the other hand, this computer acquires and stores tomographic images from an external device, such as an OCT device and a database, or a storage medium, and performs the above analytical processing on these tomographic images.

MODIFIED EXAMPLES

The configuration described above is merely one example for favorably implementing the present invention. Therefore, it is possible to properly make arbitrary modification within the scope of the present invention.

In the above embodiment, cases have been described in which analytical processing is performed on tomographic images (two-dimensional images) of a fundus, but it is also possible to perform similar analytical processing on three-dimensional images to generate similar morphological information. This type of fundus analyzing apparatus has a configuration similar to that of the above embodiment. The fundus analyzing apparatus of the present variation is described below with reference to the above embodiment (in particular, FIG. 3 and FIG. 4).

The storage 212 (storage means) of the fundus analyzing apparatus of the present variation stores three-dimensional images depicting the layer structures of the fundus Ef. The three-dimensional images may be formed by a three-dimensional image forming part 231 (three-dimensional forming means), or may be acquired from an external device.

Based on the pixel values of the pixels (voxels, etc.) of a three-dimensional image, the layer-region identifying part 233 (layer-region identification means) of the analytical processor 232 identifies the layer region in the three-dimensional image that corresponds to the pigment layer of the retina. The identified layer region is a curved surface (that may include several singularities).

In the present variation, a curved-surface calculator (curved-surface calculation means) is provided instead of the curve calculator 234 of the above embodiment. Based on the shape of the layer region identified by the layer-region identifying part 233, the curved-surface calculator obtains a convex curved surface (standard curved surface) in the direction of depth (+z direction) of the fundus Ef. This process may be executed by, for example, using the least-squares method as in the above embodiment, obtaining coefficients by substituting coordinate values into the equation of the quadric surface, or changing the coefficient parameters of the quadric surface to obtain an appropriate quadric surface.

Next, based on the layer region identified by the layer-region identifying part 233 and the curved surface obtained by the curved-surface calculator, the protrusion-region identifying part 235 (protrusion-region identification means) identifies protrusion regions where the layer region protrudes toward the opposite direction (−z direction) from the direction of depth of the fundus Ef.

Next, the morphological-information generating part 236 (morphological-information generation means) generates morphological information representing the morphology of the protrusion regions identified by the protrusion-region identifying part 235. For the morphological information, the quantity, size and distribution of drusen (connected components of protrusion regions), or a representative tomographic image or a composite image, etc. may be presented in a manner similar to the above embodiment, and it is also possible to present a pseud-three-dimensional image obtained by rendering the three-dimensional image.

According to this type of variation, as in the above embodiment, it is possible to individually determine each protruding part of the pigment layer of the retina that may be drusen, and it is therefore possible to detect even small drusen. Moreover, because the configuration is one in which protrusion regions characteristic of drusen are identified based on a three-dimensional image, it is possible to effectively detect drusen.

Furthermore, in the present variation, because three-dimensional image processing is executed, the resources used for processing increase compared to the above embodiment, which executes two-dimensional image processing. On the other hand, the present variation has the advantages of being able to determine the three-dimensional morphology of drusen with higher precision and higher accuracy. However, in the above embodiment, by reducing the interval between scanning lines, it is possible to improve the precision and accuracy of drusen detection or to improve the precision and accuracy of determining the morphology of drusen.

Another variation will be described. In the above embodiment and variation, (protrusion regions believed to be) drusen is detected based on the distance between the layer region corresponding to the pigment layer of the retina and a standard curve or standard curved surface, but a configuration may be used in which an image region (referred to as the "membrane region") corresponding to the Brusch's membrane is detected by, for example, improving the sensitivity of the OCT measurements, and detecting drusen based on the distance between the layer region and the membrane region. Because drusen occurs between the Brusch's membrane and the pigment layer of the retina, by executing the processing according to the present variation, it becomes possible to determine the morphology of the drusen with higher precision and higher accuracy.

Furthermore, in the above embodiment, instead of the Brusch's membrane, which is difficult to detect from OCT images, a standard curve or a standard curved surface that resembles the morphology of the pigment layer of the retina in a state in which no drusen (protrusions) is present is used.

As yet another variation, it is possible to identify the layer region corresponding to the pigment layer of the retina from OCT images, and attempt to identify the membrane region corresponding to the Brusch's membrane. If the membrane region is identified, protrusion regions are identified based on the distance between the membrane region and the layer region and morphological information is generated. On the other hand, if identification of the membrane layer fails, a standard curve (or standard curved surface) is obtained as in the above embodiment, protrusion regions are identified based on the layer region and the standard curve (or the standard curved surface), and morphological information is generated.

According to the present variation, the morphology of the drusen can be determined with higher precision and higher accuracy if the membrane region is identified, and if the membrane region is not identified, the morphology of the drusen can be determined by using the standard curve (or standard curved surface).

In the above embodiment, the position of the reference mirror 114 is changed to change the difference in optical path length between the optical path of the signal light LS and the optical path of the reference light LR, but the method of changing the difference in optical path length is not limited to this. For example, it is possible to change the difference in optical path length by moving the retinal camera unit 2 or the OCT unit 100 relative to the subject eye E and changing the optical path length of the signal light LS. Moreover, particularly if the object being measured is not a biological region, it is also effective to change the difference in optical path length by moving the object being measured in the depth direction (z-axis direction).

[Fundus Analyzing Program]

A fundus analyzing program of the present embodiment will now be described. This fundus analyzing program causes a computer including a storage means that stores a plurality of tomographic images that each depicts the layer structure of a fundus to execute the operations described below. Examples of this computer include the arithmetic and control unit of the above embodiment. This fundus analyzing program may be stored in the computer itself, or may be stored in a server, etc. that is communicably connected to the computer.

The operations executed by the computer based on this fundus analyzing program will now be described. First, the computer reads out each tomographic image stored in the storage means, and in a manner similar to the layer-region identifying part 233 of the above embodiment, identifies the layer region in the tomographic region that corresponds to the pigment layer of the retina based on the pixel values of the pixels in the tomographic image. Next, in a manner similar to the curve calculator 234 of the above embodiment, the computer obtains a convex curve (standard curve) in the direction of depth of the fundus based on the shape of the identified layer region. Next, in a manner similar to the protrusion-region identifying part 235 of the above embodiment, based on the layer region and the standard curve, the computer identifies protrusion regions where the layer region protrudes toward the opposite direction from the direction of depth of the fundus. Then, in a manner similar to the morphological-information generating part 236 of the above embodiment, the computer generates morphological information representing the morphology of the identified protrusion regions. The computer display outputs or print outputs the generated morphological information.

According to this type of fundus analyzing program, as with the above embodiment, it is possible to individually determine each protruding part in the pigment layer of the retina that may be drusen, and it is therefore possible to detect even small drusen. Moreover, because the configuration is one in which protrusion regions characteristic of drusen are identified based on tomographic images, it is possible to effectively detect drusen.

Another fundus analyzing program of the present embodiment will now be described. This fundus analyzing program causes a computer including a storage means that stores three-dimensional images depicting the layer structures of a fundus to execute the operations described below. Examples of the computer include the arithmetic and control unit of the above variation.

The operations executed by the computer based on this fundus analyzing program will now be described. First, the computer reads out a three-dimensional image stored in the storage means, and in a manner similar to the layer-region identifying part 233 of the above variation, identifies the layer region in the three-dimensional image that corresponds to the pigment layer of the retina based on the pixel values of the pixels in the three-dimensional image. Next, in a manner similar to the curved-surface calculator of the above variation, the computer obtains a convex curved surface (standard curved surface) in the direction of depth of the fundus based on the shape of the identified layer region. Next, in a manner similar to the protrusion-region identifying part 235 of the above variation, based on the layer region and the standard curved surface, the computer identifies protrusion regions where the layer region protrudes in the opposite direction from the direction of depth of the fundus. Then, in a manner similar to the morphological-information generating part 236 of the above variation, the computer generates morphological information representing the morphology of the identified protrusion region. The computer display outputs or print outputs the generated morphological information.

According to this type of fundus analyzing program, as with the above variation, it is possible to individually determine each protruding part in the pigment layer of the retina that may be drusen, and it is therefore possible to detect even small drusen. Moreover, because the configuration is one in which protrusion regions characteristic of drusen are identified based on a three-dimensional image, it is possible to effectively detect drusen.

The above fundus analyzing program may be configured to cause the computer to also execute the various processes described in the above embodiments and variations.

The above fundus analyzing program can be stored in any kind of recording medium that can be read by a computer. As this recording medium, for example, an optical disk, a magneto-optic disk (CD-ROM, DVD-RAM, DVD-ROM, MO, and so on), and a magnetic storage (a hard disk, a floppy disk (TM), ZIP, and so on) can be used. Moreover, it is possible to store into a storing device such as a hard disk drive and a memory.

Besides, it is possible to transmit/receive this program through a network such as internet or LAN etc.

[Fundus Analyzing Method]

The fundus analyzing method of the present invention will now be described. This fundus analyzing method analyzes multiple tomographic images that depict each layer structure of a fundus, and is configured to include the following steps.

In the first step, for each of the multiple tomographic images, based on the pixel values of the pixels in the tomographic image, the layer region in the tomographic image that corresponds to the pigment layer of the retina is identified. Next, in the second step, based on the shape of the identified layer region, a convex curve (standard curve) in the direction of depth of the fundus is obtained. Next, in the third step, based on the layer region and the standard curve, protrusion regions where the layer region protrudes in the opposite direction from the direction of depth of the fundus are identified. Then, in the fourth step, morphological information representing the morphology of the identified protrusion regions is generated.

According to this type of fundus analyzing method, as with the above embodiments, it is possible to individually determine each protruding part in the pigment layer of the retina that may be drusen, and it is therefore possible to detect even small drusen. Moreover, because the configuration is one in which protrusion regions characteristic of drusen are identified based on tomographic images, it is possible to effectively detect drusen.

Another fundus analyzing method of the present invention will now be described. This fundus analyzing method analyzes three-dimensional images depicting the layer structures of a fundus, and is configured by including the following steps.

In the first step, based on the pixel values of the pixels of a three-dimensional image, the layer region in the three-dimensional image that corresponds to the pigment layer of the retina is identified. Next, in the second step, based on the shape of the identified layer region, a convex curved surface (standard curved surface) in the direction of depth of the fundus is obtained. Next, in the third step, based on the layer region and the standard curved surface, protrusion regions where the layer region protrudes in the opposite direction from the direction of depth of the fundus are identified. Then, in the fourth step, morphological information representing the morphology of the identified protrusion regions is generated.

According to this type of fundus analyzing method, as with the above variations, it is possible to individually determine each protruding area in the pigment layer of the retina that may be drusen, and it is therefore possible to detect even small drusen. Moreover, because the configuration is one in which protrusion regions characteristic of drusen are identified based on a three-dimensional image, it is possible to effectively detect drusen.

The fundus analyzing method of the present embodiment may further include steps for executing the various processes described in the above embodiments and variations.

EXPLANATION OF THE SYMBOLS

1 Fundus analyzing apparatus
2 Retinal camera unit
10 Illumination optical system
30 Imaging optical system
43, 44 Galvano mirror
70 Scan drive
100 OCT unit
101 Light source unit
114 Reference mirror
118 Diffraction grating
120 CCD image sensor
130 Reference driver
200 Arithmetic and control unit
210 Controller
211 Main controller
212 Storage
220 Image forming part
230 Image processor
231 Three-dimensional image forming part
232 Analytical processor
233 Layer-region identifying part
234 Curve calculator
235 Protrusion-region identifying part
236 Morphological-information generating part
240 Display
250 Operation part
300 Layer region 320 Standard curve (quadratic curve)
330, 340, T Protrusion region
400 Distribution image
500 Analysis-results display screen
E Subject eye
Ef Fundus
G Tomographic image, representative tomographic image
Tk Connected component

What is claimed is:

1. A fundus analyzing apparatus comprising:
a storage means that stores a plurality of tomographic images that each depict layer structures of a fundus;
a layer-region identification means that, based on the pixel values of the pixels of each of said stored tomographic images, identifies the layer region in the tomographic image that corresponds to the pigment layer of the retina;
a curve calculation means that, based on the shape of said identified layer region, obtains a convex curve in the direction of depth of said fundus;
a protrusion-region identification means that, based on said identified layer region and said obtained curve, identifies protrusion regions where said layer region protrudes in the opposite direction from said direction of depth; and
a morphological-information generation means that generates morphological information representing the morphology of the identified protrusion regions.

2. A fundus analyzing apparatus according to claim 1, wherein
said curve calculation means includes a characteristic-region identification means that identifies a plurality of characteristic regions within said layer region based on the shape of the layer region identified by said layer-region identification means, and obtains said curve based on the identified plurality of characteristic regions.

3. A fundus analyzing apparatus according to claim 2, wherein
said characteristic-region identification means identifies the deepest region in said layer region in said direction of depth based on the shape of said layer region and defines it as said characteristic region, obtains a straight line that passes through said deepest region and comes into contact with said layer region, and defines points of contact between said layer region and said straight line as said characteristic regions.

4. A fundus analyzing apparatus according to claim 3, wherein
said characteristic-region identification means sequentially identifies said points of contact by rotating the straight line passing through said deepest region while keeping said deepest region in the center.

5. A fundus analyzing apparatus according to claim 3, wherein
said characteristic-region identification means rotates the straight line passing through said deepest region while keeping said deepest region in the center to identify points of contact, and rotates a straight line passing through the identified points of contact while keeping this point of contact in the center to identify more points of contact.

6. A fundus analyzing apparatus according to claim 2, wherein
said curve calculation means obtains a quadratic curve based on said identified plurality of characteristic regions as said curve.

7. A fundus analyzing apparatus according to claim 6, wherein
said curve calculation means obtains, through the least-squares method, the quadratic curve with the smallest difference with a broken line connecting said plurality of characteristic regions.

8. A fundus analyzing apparatus according to claim 6, wherein
said curve calculation means substitutes the respective coordinate values of said plurality of characteristic regions in a coordinate system that has been preliminarily set in said tomographic image into the formula of the quadratic curve and performs a calculation to obtain the coefficient of said formula.

9. A fundus analyzing apparatus according to claim 1, wherein
said protrusion-region identification means identifies image regions where the distance in said direction of depth between said layer region and said curve becomes equal to or greater than a prescribed threshold value as said protrusion regions.

10. A fundus analyzing apparatus according to claim 9, wherein
said protrusion-region identification means calculates the distance in said direction of depth between each point on said curve and said layer region, determines whether the calculated distances are equal to or greater than said prescribed threshold value, and identifies image regions located between a set of the points on said curve determined to be equal to or greater than said threshold value and said layer region and defines them as said protrusion regions.

11. A fundus analyzing apparatus according to claim 1, wherein
said morphological-information generation means includes: a distribution-image forming means that, based on the protrusion regions identified for each said tomographic image by said protrusion-region identification means, forms a distribution image representing the distribution state of protrusion regions in a plane orthogonal to said direction of depth; and a connected-component identification means that, based on the pixel values of the pixels of the formed distribution image, identifies connected components in the protrusion regions in the distribution image, and
said morphological-information generation means generates said morphological information based on the identified connected components.

12. A fundus analyzing apparatus according to claim 11, wherein
said morphological-information generation means includes a counting means that counts the number of connected components identified by said connected-component identification means, and generates said morphological information based on the number obtained through said count.

13. A fundus analyzing apparatus according to claim 11, wherein
said morphological-information generation means includes a size calculation means that calculates the size of each connected component identified by said connected-component identification means, and generates size distribution information representing the distribution of said calculated sizes and defines it as said morphological information.

14. A fundus analyzing apparatus according to claim 13, wherein
said size calculation means calculates the area of each said connected component as said size.

15. A fundus analyzing apparatus according to claim 13, wherein
said size calculation means calculates the diameter of each said connected component as said size.

16. A fundus analyzing apparatus according to claim 15, wherein
said size calculation means calculates the area of each said connected component, and obtains the diameter of a circle having the calculated area and defines it as the diameter of the connected component.

17. A fundus analyzing apparatus according to claim 13, wherein
said size calculation means calculates the volume of each said connected component as said size.

18. A fundus analyzing apparatus according to claim 17, wherein
said size calculation means calculates the volume of the connected components by integrating the distance in said direction of depth between said layer region and said curve across each said connected component.

19. A fundus analyzing apparatus according to claim 11, wherein
said storage means also stores captured images of said fundus, and
said morphological-information generation means forms a composite image of said captured image and said distribution image, and defines it as said morphological information.

20. A fundus analyzing apparatus according to claim 1, further comprising:
an optical system that divides low-coherence light into a signal light and a reference light, overlaps said signal light that has passed through the fundus of a subject eye and the reference light that has passed through a reference light path, and generates and detects interference light; and
an image forming means that, based on the detection results of said interference light, forms a plurality of tomographic images of said fundus, wherein
said storage means stores the plurality of tomographic images formed by said image forming means.

21. A fundus analyzing apparatus according to claim 20, wherein
said optical system includes a scanning means that sequentially scans the irradiation positions of said signal light on said fundus along a plurality of scanning lines, and
said image forming means forms a tomographic image along each of said plurality of scanning lines based on the detection results of said interference light from said optical system.

22. A fundus analyzing apparatus comprising:
a storage means that stores three-dimensional images depicting layer structures of a fundus;
a layer-region identification means that, based on the pixel values of the pixels of said stored three-dimensional images, identifies the layer region in said three-dimensional image that corresponds to the pigment layer of the retina;
a curved-surface calculation means that, based on the shape of said identified layer region, obtains a convex curved surface in the direction of depth of said fundus;
a protrusion-region identification means that, based on said identified layer region and said obtained curved surface, identifies protrusion regions where said layer region protrudes in the opposite direction from said direction of depth; and
a morphological-information generation means that generates morphological information representing the morphology of the identified protrusion region.

23. A fundus analyzing apparatus according to claim 22, further comprising:
an optical system that divides low-coherence light into a signal light and a reference light, overlaps said signal light that has passed through the fundus of a subject eye and the reference light that has passed through a reference light path, and generates and detects interference light;
an image forming means that, based on the detection results of said interference light, forms a plurality of tomographic images of said fundus; and
a three-dimensional image forming means that forms three-dimensional images based on said plurality of formed tomographic images, wherein
said storage means stores the three-dimensional images formed by said three-dimensional image forming means.

24. A fundus analyzing apparatus according to claim 23, wherein
said optical system includes a scanning means that sequentially scans the irradiation positions of said signal light on said fundus along a plurality of scanning lines, and
said image forming means forms a tomographic image along each of said plurality of scanning lines based on the detection results of said interference light from said optical system.

25. A fundus analyzing method that analyzes a plurality of tomographic images that each depict layer structures of a fundus, comprising the steps of:
for each of said plurality of tomographic images, identifying the layer region in the tomographic image that corresponds to the pigment layer of the retina based on the pixel values of the pixels of the tomographic image;
obtaining, based on the shape of said identified layer region, a convex curve in the direction of depth of said fundus;
identifying, based on said identified layer region and said obtained curve, protrusion regions where said layer region protrudes in the opposite direction from said direction of depth; and
generating morphological information representing the morphology of the identified protrusion regions.

26. A fundus analyzing method that analyzes three-dimensional images depicting layer structures of a fundus, comprising the steps of:
identifying, based on the pixel values of the pixels of said three-dimensional image, the layer region in said three-dimensional image that corresponds to the pigment layer of the retina;
obtaining, based on the shape of said identified layer region, a convex curved surface in the direction of depth of said fundus;
identifying, based on said identified layer region and said obtained curved surface, protrusion regions where said layer region protrudes in the opposite direction from said direction of depth; and
generating morphological information representing the morphology of the identified protrusion regions.

* * * * *